(12) United States Patent
Fujiwara et al.

(10) Patent No.: US 10,317,360 B2
(45) Date of Patent: Jun. 11, 2019

(54) LIQUID SAMPLE MEASUREMENT DEVICE, LIQUID SAMPLE MEASUREMENT METHOD, AND BIOSENSOR

(71) Applicant: PHC HOLDINGS CORPORATION, Tokyo (JP)

(72) Inventors: Masaki Fujiwara, Ehime (JP); Tomohiro Yamamoto, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 254 days.

(21) Appl. No.: 14/782,216

(22) PCT Filed: Apr. 18, 2014

(86) PCT No.: PCT/JP2014/002204
§ 371 (c)(1),
(2) Date: Oct. 2, 2015

(87) PCT Pub. No.: WO2014/174815
PCT Pub. Date: Oct. 30, 2014

(65) Prior Publication Data
US 2016/0025674 A1  Jan. 28, 2016

(30) Foreign Application Priority Data
Apr. 26, 2013 (JP) .................. 2013-094263

(51) Int. Cl.
*G01N 27/30* (2006.01)
*G01N 27/327* (2006.01)

(52) U.S. Cl.
CPC ......... *G01N 27/3274* (2013.01); *G01N 27/30* (2013.01); *G01N 27/3271* (2013.01)

(58) Field of Classification Search
CPC . G01N 27/3274; G01N 27/30; G01N 27/3271
See application file for complete search history.

(56) References Cited

U.S. PATENT DOCUMENTS

2004/0154932 A1  8/2004  Deng et al.
2004/0157338 A1  8/2004  Burke et al.
(Continued)

FOREIGN PATENT DOCUMENTS

CN    1558224    12/2004
CN    1938590    3/2007
(Continued)

OTHER PUBLICATIONS

International search report for International application No. PCT/JP2014/002204, dated Jul. 22, 2014 (4 pages).
(Continued)

*Primary Examiner* — Bethany L Martin
(74) *Attorney, Agent, or Firm* — Hamre, Schumann, Mueller & Larson, P.C.

(57) ABSTRACT

It is intended to provide, for example, a liquid sample measurement device capable of measuring the amounts of components of a liquid with a high accuracy. A first voltage is applied to an electrode pair 21, 22, which composes a biosensor 1, to obtain, a first response value, a second voltage is applied to an electrode pair 23, 24, which composes the biosensor 1, to obtain a second response value, and a current that is generated when a third voltage is applied to an electrode pair 23, 27, which composes the biosensor 1, is detected to obtain a third response value. A liquid sample measurement device 6 uses the first response value, the second response value, and the third response value to obtain the concentration of glucose and the amount of blood cells of blood as well as the value equivalent to the temperature of the biosensor 1.

4 Claims, 38 Drawing Sheets

(56) References Cited

U.S. PATENT DOCUMENTS

| | | | |
|---|---|---|---|
| 2007/0138026 A1* | 6/2007 | Fujiwara | A61B 5/14546 |
| | | | 205/777.5 |
| 2011/0027816 A1* | 2/2011 | Fujiwara | G01N 27/3274 |
| | | | 435/25 |
| 2011/0203942 A1 | 8/2011 | Uchiyama | |
| 2011/0272294 A1 | 11/2011 | Fujiwara | |

FOREIGN PATENT DOCUMENTS

| | | |
|---|---|---|
| JP | 2009258129 | 11/2009 |
| JP | 2011137769 | 7/2011 |
| WO | 2009/042631 | 4/2009 |
| WO | 2010061629 | 6/2010 |
| WO | 2010087191 | 8/2010 |
| WO | 2011/081211 | 7/2011 |

OTHER PUBLICATIONS

Extended European Search Report issued in corresponding European application No. 14788169.2, dated May 3, 2016, 6 pages.
Office Action issued in corresponding Chinese Patent Application No. 201480023276.X, dated Mar. 15, 2017, 12 pages.
Office Action issued in corresponding Japanese Patent Application No. 2015-513557, dated Nov. 30, 2017, 5 pages with translation.
Office Action issued in corresponding Chinese Patent Application No. 201480023276.X, dated Aug. 23, 2017, 8 pages with English translation.

* cited by examiner

| Glucose | Hct | First Response Value | Second Response Value | Second Response Value | Second Response Value |
|---|---|---|---|---|---|
| 100mg/dl | Hct25 | 120 | 1250 | | |
| | Hct45 | 100 | 1000 | | |
| | Hct65 | 80 | 750 | | |
| 200mg/dl | Hct25 | 250 | | 1250 | |
| | Hct45 | 200 | | 1000 | |
| | Hct65 | 150 | | 750 | |
| 110mg/dl | Hct25 | 133.1 | | | 1250 |
| | Hct45 | 110 | | | 1000 |
| | Hct65 | 86.9 | | | 750 |

| Order Designation | Working Electrode Designation | Counter Electrode 1 | Counter Electrode 2 | Counter Electrode 3 | Counter Electrode 4 | Counter Electrode 5 | Applied Voltage | Spotting Current | Time (s) | Total Time |
|---|---|---|---|---|---|---|---|---|---|---|
| T | Working Electrode 1 | D | E | | | | 500 | 0.05 | 0.8 | 0.8 |
| S | Working Electrode 2 | C | D | | | | 350 | | 0.2 | 1.0 |
| S | Working Electrode 1 | C | D | E | | | 350 | | 0.5 | 1.5 |
| S | Working Electrode 2 | A | G | | | | 2500 | | 0.2 | 1.7 |
| S | Working Electrode 1 | C | D | E | | | 350 | | 0.6 | 2.3 |
| S | Working Electrode 2 | C | D | E | | | 350 | | 0.2 | 2.5 |
| S | Working Electrode 1 | A | F | | | | 2000 | | 1.3 | 3.8 |
| S | Working Electrode 2 | C | D | E | | | 350 | | 0.2 | 4.0 |
| S | Working Electrode 1 | C | D | E | | | 350 | | 0.5 | 4.5 |
| S | Working Electrode 2 | A | G | | | | 2500 | | 0.2 | 4.7 |
| S | Working Electrode 1 | C | D | E | | | 350 | | 0.6 | 5.3 |
| S | Working Electrode 2 | C | D | E | | | 350 | | 0.2 | 5.5 |
| S | Working Electrode 1 | A | G | | | | 2500 | | 1.5 | 7.0 |
| S | Working Electrode 2 | C | D | E | | | 350 | | 1.0 | 8.0 |
| S | Working Electrode 1 | C | D | E | G | | 2000 | | | |

FIG. 9

| Order Designation | Working Electrode Designation | Counter Electrode 1 | Counter Electrode 2 | Counter Electrode 3 | Counter Electrode 4 | Counter Electrode 5 | Counter Electrode 6 | Counter Electrode 7 | Applied Voltage | Spotting Current | Time (s) | Total Time |
|---|---|---|---|---|---|---|---|---|---|---|---|---|
| T | Working Electrode 1 | E | | | | | | | 500 | 0.05 | 0.8 | 0.8 |
| S | Working Electrode 2 | D | | | | | | | 350 | | 0.2 | 1.0 |
| S | Working Electrode 1 | G | E | | | | | | 2500 | | 0.5 | 1.5 |
| S | Working Electrode 2 | D | | | | | | | 350 | | 0.2 | 1.7 |
| S | Working Electrode 1 | A | F | E | | | | | 2500 | | 0.6 | 2.3 |
| S | Working Electrode 2 | D | | | | | | | 350 | | 0.2 | 2.5 |
| S | Working Electrode 1 | A | G | E | | | | | 2500 | | 1.3 | 3.8 |
| S | Working Electrode 2 | D | | | | | | | 350 | | 0.2 | 4.0 |
| S | Working Electrode 1 | A | G | D | E | | | | 2500 | | 0.5 | 4.5 |
| S | Working Electrode 2 | D | | | | | | | 350 | | 0.2 | 4.7 |
| S | Working Electrode 1 | F | A | D | E | | | | 2500 | | 0.6 | 5.3 |
| S | Working Electrode 2 | D | | | | | | | 350 | | 0.2 | 5.5 |
| S | Working Electrode 1 | A | G | D | E | | | | 2500 | | 1.5 | 7.0 |
| S | Working Electrode 1 | G | D | E | G | | | | 2000 | | 1.0 | 8.0 |

| Order Designation | Working Electrode Designation | | Counter Electrode Designation | | | | | | | Applied Voltage | Spotting Current | Time (s) | Total Time |
|---|---|---|---|---|---|---|---|---|---|---|---|---|---|
| | | | Counter Electrode 1 | Counter Electrode 2 | Counter Electrode 3 | Counter Electrode 4 | Counter Electrode 5 | Counter Electrode 6 | Counter Electrode 7 | | | | |
| T | Working Electrode 1 | D | E | | | | | | | 100 | 0.05 | 0.8 | 0.8 |
| | Working Electrode 2 | | | | | | | | | | | | |
| S | Working Electrode 1 | C | D | E | | | | | | 350 | | 0.2 | 1.0 |
| | Working Electrode 2 | | | | | | | | | | | | |
| S | Working Electrode 1 | C | D | E | | | | | | 350 | | 0.5 | 1.5 |
| | Working Electrode 2 | A | G | | | | | | | 2500 | | | |
| S | Working Electrode 1 | C | D | E | | | | | | 350 | | 0.5 | 2.0 |
| | Working Electrode 2 | | | | | | | | | | | | |
| S | Working Electrode 1 | C | D | E | | | | | | 350 | | 0.3 | 2.3 |
| | Working Electrode 2 | A | F | | | | | | | 2000 | | | |
| S | Working Electrode 1 | C | D | E | | | | | | 350 | | 0.2 | 2.5 |
| | Working Electrode 2 | | | | | | | | | | | | |
| S | Working Electrode 1 | C | D | E | | | | | | 350 | | 1.3 | 3.8 |
| | Working Electrode 2 | A | G | | | | | | | 2500 | | | |
| S | Working Electrode 1 | C | D | E | | | | | | 350 | | 0.2 | 4.0 |
| | Working Electrode 2 | | | | | | | | | | | | |
| S | Working Electrode 1 | C | D | E | | | | | | 350 | | 0.5 | 4.5 |
| | Working Electrode 2 | A | G | | | | | | | 2300 | | | |
| S | Working Electrode 1 | C | D | E | | | | | | 350 | | 0.5 | 5.0 |
| | Working Electrode 2 | | | | | | | | | | | | |
| S | Working Electrode 1 | C | D | E | | | | | | 350 | | 0.3 | 5.3 |
| | Working Electrode 2 | F | A | | | | | | | 2000 | | | |
| S | Working Electrode 1 | C | D | E | | | | | | 350 | | 0.2 | 5.5 |
| | Working Electrode 2 | | | | | | | | | | | | |
| S | Working Electrode 1 | C | D | E | | | | | | 350 | | 1.5 | 7.0 |
| | Working Electrode 2 | A | G | | | | | | | 2300 | | | |
| S | Working Electrode 1 | C | D | E | | | | | | 1200 | | 1.0 | 8.0 |
| | Working Electrode 2 | | | | | | | | | | | | |

| Order | Working Electrode Designation | Counter Electrode 1 | Counter Electrode 2 | Counter Electrode 3 | Counter Electrode 4 | Counter Electrode 5 | Counter Electrode 6 | Counter Electrode 7 | Applied Voltage | Spotting Current | Time (s) | Total Time |
|---|---|---|---|---|---|---|---|---|---|---|---|---|
| T | Working Electrode 1 | D | E | | | | | | 500 | 0.05 | | |
| | Working Electrode 2 | | | | | | | | | | | |
| S | Working Electrode 1 | C | D | E | | | | | 350 | | 0.5 | 0.5 |
| | Working Electrode 2 | | | | | | | | | | | |
| S | Working Electrode 1 | C | D | E | | | | | 350 | | 0.2 | 0.7 |
| | Working Electrode 2 | A | G | | | | | | 2500 | | | |
| S | Working Electrode 1 | C | D | E | | | | | 350 | | 0.5 | 1.2 |
| | Working Electrode 2 | | | | | | | | | | | |
| S | Working Electrode 1 | C | D | E | | | | | 350 | | 0.2 | 1.4 |
| | Working Electrode 2 | A | F | | | | | | 2000 | | | |
| S | Working Electrode 1 | C | D | E | | | | | 350 | | 0.5 | 1.9 |
| | Working Electrode 2 | | | | | | | | | | | |
| S | Working Electrode 1 | C | D | E | | | | | 350 | | 0.2 | 2.1 |
| | Working Electrode 2 | A | G | | | | | | 2500 | | | |
| S | Working Electrode 1 | C | D | E | | | | | 350 | | 0.5 | 2.6 |
| | Working Electrode 2 | | | | | | | | | | | |
| S | Working Electrode 1 | C | D | E | | | | | 350 | | 0.2 | 2.8 |
| | Working Electrode 2 | F | A | | | | | | 2000 | | | |
| S | Working Electrode 1 | C | D | E | | | | | 350 | | 0.5 | 3.3 |
| | Working Electrode 2 | | | | | | | | | | | |
| S | Working Electrode 1 | C | D | E | | | | | 350 | | 0.2 | 3.5 |
| | Working Electrode 2 | A | G | | | | | | 2500 | | | |
| S | Working Electrode 1 | C | D | E | | | | | 350 | | 0.5 | 4.0 |
| | Working Electrode 2 | | | | | | | | | | | |
| S | Working Electrode 1 | C | D | E | | | | | 350 | | 0.2 | 4.2 |
| | Working Electrode 2 | F | A | | | | | | 2000 | | | |
| S | Working Electrode 1 | C | D | E | | | | | 350 | | 0.5 | 4.7 |
| | Working Electrode 2 | | | | | | | | | | | |
| S | Working Electrode 1 | C | D | E | | | | | 350 | | 0.2 | 4.9 |
| | Working Electrode 2 | A | G | | | | | | 2500 | | | |
| S | Working Electrode 1 | C | D | E | | | | | 350 | | 0.5 | 5.4 |
| | Working Electrode 2 | | | | | | | | | | | |
| S | Working Electrode 1 | C | D | E | | | | | 350 | | 0.2 | 5.6 |
| | Working Electrode 2 | F | A | | | | | | 2000 | | | |
| S | Working Electrode 1 | C | D | E | | | | | 350 | | 0.5 | 6.1 |
| | Working Electrode 2 | | | | | | | | | | | |
| S | Working Electrode 1 | C | D | E | | | | | 350 | | 0.2 | 6.3 |
| | Working Electrode 2 | A | G | | | | | | 2500 | | | |
| S | Working Electrode 1 | C | D | E | | | | | 350 | | 3.7 | 10.0 |
| | Working Electrode 2 | | | | | | | | | | | |

FIG. 29

| Order designation | Working Electrode Designation | Counter Electrode 1 | Counter Electrode 2 | Counter Electrode 3 | Counter Electrode 4 | Counter Electrode 5 | Counter Electrode 6 | Counter Electrode 7 | Applied Voltage | Spotting Current | Time (s) | Total Time |
|---|---|---|---|---|---|---|---|---|---|---|---|---|
| T | Working Electrode 1 | D | E | | | | | | 500 | 0.05 | | |
|   | Working Electrode 2 | | | | | | | | | | | | |
| S | Working Electrode 1 | C | D | E | | | | | 350 | | 0.5 | 0.5 |
|   | Working Electrode 2 | | | | | | | | | | | | |
| S | Working Electrode 1 | C | D | E | | | | | 350 | | 0.2 | 0.7 |
|   | Working Electrode 2 | A | G | | | | | | 2500 | | | |
| S | Working Electrode 1 | C | D | E | | | | | 350 | | 0.5 | 1.2 |
|   | Working Electrode 2 | | | | | | | | | | | | |
| S | Working Electrode 1 | C | D | E | | | | | 350 | | 0.2 | 1.4 |
|   | Working Electrode 2 | A | F | | | | | | 2000 | | | |
| S | Working Electrode 1 | C | D | E | | | | | 350 | | 0.5 | 1.9 |
|   | Working Electrode 2 | | | | | | | | | | | | |
| S | Working Electrode 1 | C | D | E | | | | | 350 | | 0.2 | 2.1 |
|   | Working Electrode 2 | A | G | | | | | | 2500 | | | |
| S | Working Electrode 1 | C | D | E | | | | | 350 | | 0.5 | 2.6 |
|   | Working Electrode 2 | | | | | | | | | | | | |
| S | Working Electrode 1 | C | D | E | | | | | 350 | | 0.2 | 2.8 |
|   | Working Electrode 2 | F | A | | | | | | 2000 | | | |
| S | Working Electrode 1 | C | D | E | | | | | 350 | | 0.5 | 3.3 |
|   | Working Electrode 2 | | | | | | | | | | | | |
| S | Working Electrode 1 | C | D | E | | | | | 350 | | 0.2 | 3.5 |
|   | Working Electrode 2 | A | G | | | | | | 2500 | | | |
| S | Working Electrode 1 | C | D | E | | | | | 350 | | 0.5 | 4.0 |
|   | Working Electrode 2 | | | | | | | | | | | | |
| S | Working Electrode 1 | C | D | E | | | | | 350 | | 0.2 | 4.2 |
|   | Working Electrode 2 | F | A | | | | | | 2000 | | | |
| S | Working Electrode 1 | C | D | E | | | | | 350 | | 0.5 | 4.7 |
|   | Working Electrode 2 | | | | | | | | | | | | |
| S | Working Electrode 1 | C | D | E | | | | | 350 | | 0.2 | 4.9 |
|   | Working Electrode 2 | A | G | | | | | | 2500 | | | |
| S | Working Electrode 1 | C | D | E | | | | | 350 | | 0.5 | 5.4 |
|   | Working Electrode 2 | | | | | | | | | | | | |
| S | Working Electrode 1 | C | D | E | | | | | 350 | | 0.2 | 5.6 |
|   | Working Electrode 2 | F | A | | | | | | 2000 | | | |
| S | Working Electrode 1 | C | D | E | | | | | 350 | | 0.5 | 6.1 |
|   | Working Electrode 2 | | | | | | | | | | | | |
| S | Working Electrode 1 | C | D | E | | | | | 350 | | 0.2 | 6.3 |
|   | Working Electrode 2 | A | G | | | | | | 2500 | | | |
| S | Working Electrode 1 | C | D | E | | | | | 350 | | 3.7 | 10.0 |
|   | Working Electrode 2 | | | | | | | | | | | | |

FIG. 32

| Order Designation | Working Electrode Designation | Counter Electrodes Designation ||||||| Applied Voltage | Shooting Current | Time (s) | Total Time |
| --- | --- | --- | --- | --- | --- | --- | --- | --- | --- | --- | --- | --- |
| | | Counter Electrode 1 | Counter Electrode 2 | Counter Electrode 3 | Counter Electrode 4 | Counter Electrode 5 | Counter Electrode 6 | Counter Electrode 7 | | | | |
| T | Working Electrode 1 | D | E | | | | | | 500 | 0.05 | | |
| | Working Electrode 2 | | | | | | | | | | | |
| S | Working Electrode 1 | C | D | E | | | | | 350 | | 0.5 | 0.5 |
| | Working Electrode 2 | | | | | | | | | | | |
| S | Working Electrode 1 | C | D | E | | | | | 350 | | 0.2 | 0.7 |
| | Working Electrode 2 | A | G | | | | | | 2500 | | | |
| S | Working Electrode 1 | C | D | E | | | | | 350 | | 0.5 | 1.2 |
| | Working Electrode 2 | | | | | | | | | | | |
| S | Working Electrode 1 | C | D | E | | | | | 350 | | 0.2 | 1.4 |
| | Working Electrode 2 | A | G | | | | | | 2000 | | | |
| S | Working Electrode 1 | C | D | E | | | | | 350 | | 0.5 | 1.9 |
| | Working Electrode 2 | | | | | | | | | | | |
| S | Working Electrode 1 | C | D | E | | | | | 350 | | 0.2 | 2.1 |
| | Working Electrode 2 | | | | | | | | | | | |
| S | Working Electrode 1 | C | D | E | | | | | 350 | | 0.5 | 2.6 |
| | Working Electrode 2 | | | | | | | | | | | |
| S | Working Electrode 1 | C | D | E | | | | | 350 | | 0.2 | 2.8 |
| | Working Electrode 2 | | | | | | | | | | | |
| S | Working Electrode 1 | C | D | E | | | | | 350 | | 0.5 | 3.3 |
| | Working Electrode 2 | | | | | | | | | | | |
| S | Working Electrode 1 | C | D | E | | | | | 350 | | 0.2 | 3.5 |
| | Working Electrode 2 | A | G | | | | | | 2500 | | | |
| S | Working Electrode 1 | C | D | E | | | | | 350 | | 0.5 | 4.0 |
| | Working Electrode 2 | | | | | | | | | | | |
| S | Working Electrode 1 | C | D | E | | | | | 350 | | 0.2 | 4.2 |
| | Working Electrode 2 | | | | | | | | | | | |
| S | Working Electrode 1 | C | D | E | | | | | 350 | | 0.5 | 4.7 |
| | Working Electrode 2 | | | | | | | | | | | |
| S | Working Electrode 1 | C | D | E | | | | | 350 | | 0.2 | 4.9 |
| | Working Electrode 2 | | | | | | | | | | | |
| S | Working Electrode 1 | C | D | E | | | | | 350 | | 0.5 | 5.4 |
| | Working Electrode 2 | | | | | | | | | | | |
| S | Working Electrode 1 | C | D | E | | | | | 350 | | 0.2 | 5.6 |
| | Working Electrode 2 | F | A | | | | | | 2000 | | | |
| S | Working Electrode 1 | C | D | E | | | | | 350 | | 0.5 | 6.1 |
| | Working Electrode 2 | | | | | | | | | | | |
| S | Working Electrode 1 | C | D | E | | | | | 350 | | 0.2 | 6.3 |
| | Working Electrode 2 | A | G | | | | | | 2500 | | | |
| S | Working Electrode 1 | C | D | E | | | | | 350 | | 3.7 | 10.0 |
| | Working Electrode 2 | | | | | | | | | | | |

FIG. 35

LIQUID SAMPLE MEASUREMENT DEVICE, LIQUID SAMPLE MEASUREMENT METHOD, AND BIOSENSOR

TECHNICAL FIELD

The present invention relates to a liquid sample measurement device, a liquid sample measurement method, and a biosensor, for measuring the amounts of the components contained in a liquid.

BACKGROUND ART

A known technique for measuring a biological sample is described in Patent Document 1 mentioned below. In Patent Document 1, a sensor chip for measuring the temperature of a blood sample is provided. A predetermined voltage is applied to the working electrode and the counter electrode of the sensor chip to measure the temperature of the blood sample. The predetermined voltage is selected to be a value that has little effect on the change in, for example, concentration of glucose. Furthermore, in this sensor chip, a voltage is applied to the same electrodes to measure, for example, the concentration of glucose of a blood sample.

PRIOR ART DOCUMENTS

Patent Documents

[Patent Document 1] WO 2010/087191 A1

DISCLOSURE OF INVENTION

Problem to be Solved by the Invention

In Patent Document 1, however, it cannot be considered that the temperature of the reaction part is detected with a high accuracy. Thus, the concentration of glucose, etc. cannot be measured with a high accuracy.

Therefore, with the above in mind, the present invention has been proposed and is intended to provide a liquid sample measurement device, a liquid sample measurement method, and a biosensor, in each of which the amounts of the components of a liquid can be measured with a high accuracy.

Means for Solving Problem

A liquid sample measurement device according to a first aspect of the present invention is a liquid sample measurement device that measures the amounts of components using a biosensor in which a liquid is introduced and then components contained in said liquid are subjected to oxidation-reduction using an oxidoreductase, wherein the liquid sample measurement device includes: a first current value measurement means that detects, as a first current value, an oxidation-reduction current that is generated by the oxidation-reduction when a first voltage is applied to a first electrode pair, which composes the biosensor; a second current value measurement means that detects, as a second current value, a current that is generated when a second voltage is applied to a second electrode pair, which composes the biosensor a control means that controls a voltage value and a voltage application period of each of the first voltage and the second voltage, that controls each measurement timing for measuring the first current value and the second current value, and that also controls the measurement timing so as to measure a third current value, which is different from the first current value and the second currant value, by the first current value measurement means; and a calculation means that calculates the amounts of a first component and a second component contained in the liquid as well as a value equivalent to the temperature of the biosensor using a set of the first current value, the second current value, and the third current value generated when the first voltage and the second voltage were applied, respectively.

A liquid sample measurement device according to a second aspect of the present invention is a liquid sample measurement device that measures the amounts of components using a biosensor in which a liquid is introduced and then components contained in said liquid are subjected to oxidation-reduction using an oxidoreductase, wherein the liquid sample measurement device includes: a first current value measurement means that detects, as a first current value, an oxidation-reduction current that is generated by the oxidation-reduction when a first voltage is applied to a first electrode pair, which composes the biosensor; a second current value measurement means that detects, as a second current value, a current that is generated when a second voltage is applied to a second electrode pair, which composes the biosensor; a third current value measurement means that detects, as a third current value, a current that is generated when a third voltage is applied to a third electrode pair, which composes the biosensor; a control means that controls a voltage value and a voltage application period of each of the first voltage, the second voltage, and the third voltage and that controls each measurement timing for measuring the first current value, the second current value, and the third current value; and a calculation means that calculates the amounts of a first component and a send component contained in the liquid as well as a value equivalent to the temperature of the biosensor using a set of the first current value, the second current value, and the third current value generated when the first voltage, the second voltage, and the third voltage were applied, respectively.

A liquid sample measurement device according to a third aspect of the present invention is a liquid sample measurement device that measures the amounts of components using a biosensor in which a liquid is introduced and then components contained in said liquid are subjected to oxidation-reduction using an oxidoreductase, wherein the liquid, sample measurement device includes: a temperature detection means that detects an ambient temperature; a first current value measurement means that detects, as a first current value, an oxidation-reduction current that is generated by the oxidation-reduction when a first voltage is applied to a first electrode pair, which composes the biosensor; a second current value measurement means that detects, as a second current value, a current that is generated when a second voltage is applied to a second electrode pair which composes the biosensor; a third current value measurement means that detects, as a third current value, a current that is generated when a third voltage is applied to a third electrode pair, which composes the biosensor; a control means that controls a voltage value and a voltage application period of each of the first voltage, the second voltage, and the third voltage, that controls each measurement timing for measuring the first current value, the second current value, and the third current value, and that also controls the measurement timing so as to measure a fourth current value, which is different from the first current value and the second current value, by the first current value measurement means; and a calculation means that calculates the amounts of a first component and a second component contained in the liquid as well as a value equivalent to the temperature of the biosensor, wherein the calculation means includes a first calculation means that calculates the amounts of the first component and the second component contained in the liquid as well as a first temperature equivalent value that is equivalent to the temperature of the biosensor using a set of the first current value, the second current value, and the fourth current value generated when the first voltage and the second voltage were applied, respectively, and a second calculation means that calculates the amounts of the first component and the second component contained in the liquid as well as a second temperature equivalent value that is equivalent to the temperature of the biosensor using a set of the first current value, the second current value, and the third current value generated when the first voltage, the second voltage, and the third voltage are applied, respectively, and the amount of the first component is recalculated based on the amount of the first component calculated by the first calculation means and the amount of the first component calculated by the second calculation means, the amount of the second component is recalculated based on the amount of the second component calculated by the first calculation means and the amount of the second component calculated by the second calculation means, and the temperature of the biosensor is recalculated based on the temperature detected by the temperature detection means as well as the first temperature equivalent, value and the second temperature equivalent value.

A liquid sample measurement device according to a fourth aspect of the present invention is the liquid sample measurement device of the above-mentioned second or third aspect, wherein the control means exerts control so that while the first voltage is applied to the first electrode pair by the first current value measurement means, the third current value is measured by the third current value measurement means.

A liquid sample measurement device according to a fifth aspect of the present invention is the liquid sample measurement device of the above-mentioned second or third aspect, wherein the control means exerts control so that after the second voltage is applied to the second electrode pair by the second current value measurement means, the third current value is measured by the third current value measurement means.

A liquid sample measurement device according to a sixth aspect of the present invention is the liquid sample measurement device of the above-mentioned first or second aspect, wherein the liquid sample measurement device includes a storage means that contains recorded data stored therein including the first current value, the second current value, and the third current value recorded per temperature and liquid containing the first component and the second component whose amounts are known, the calculation means compares the recorded data with measured data containing the first current value that was measured, the second current, value that was measured, and the third current value that was measured, to calculate the amount of the first component of the liquid from which the recorded data most approximated to said measured data was obtained, as the amount of the first component of the liquid introduced into the biosensor.

A liquid sample measurement device according to a seventh aspect of the present invention is the liquid sample measurement device of the above-mentioned second or third aspect, wherein the liquid sample measurement device includes a first storage means that contains recorded data stored therein including the first current value, the second current value, and the fourth current value recorded per temperature and liquid containing the first component and the second component whose amounts are known, the first calculation means compares the recorded data with measured data containing the first current value that was measured, the second current value that was measured, and the fourth current value that was measured, to calculate the amounts of the first component and the second component of the liquid from which the recorded data most approximated to said measured data was obtained as well as the temperature of the biosensor at which the recorded data most approximated to said measured data was obtained, as the amounts of the first component and the second component of the liquid introduced into the biosensor and the first temperature equivalent, value, and the liquid sample measurement device includes a second storage means that contains recorded data stored therein including the first current value, the second current value, and the third current value recorded per temperature and liquid containing the first component and the second component whose amounts are known, and the second calculation means compares the recorded data with measured data containing the first current value that was measured, the second current value that was measured, and the third current value that was measured, to calculate the amounts of the first component and the second component of the liquid from which the recorded data most approximated to said measured data was obtained as well as the temperature of the biosensor at which the recorded data most approximated to said measured data was obtained, as the amounts of the first component and the second component of the liquid introduced into the biosensor and the second temperature equivalent value.

A liquid sample measurement device according to an eighth aspect of the present invention is the liquid sample measurement device of the second or third aspect, wherein the third electrode pair is composed of a first electrode, which does not contact the liquid introduced into the biosensor and an electrode, which does not contact the liquid, selected from the second electrode pair of the second current value measurement means.

A liquid sample measurement method according to a ninth aspect of the present invention is a liquid sample measurement method in which the amounts of components are measured using a biosensor in which a liquid is introduced and then components contained in said liquid are subjected to oxidation-reduction using an oxidoreductase, wherein the liquid sample measurement method includes a first current value measurement step for detecting, as a first current value, an oxidation-reduction current that is generated by the oxidation-reduction when a first voltage is applied to a first electrode pair, which composes the biosensor and a second current value measurement step for detecting, as a second current value, a current that is generated when a second voltage is applied to a second electrode pair, which composes the biosensor, a voltage value and a voltage application period of each of the first voltage and the second voltage are controlled, each measurement timing for measuring the first current value and the second current value is controlled, the measurement timing is controlled so that a third current value that is different from the first current value and the second current value is measured in the first current value measurement step, and the amounts of a first component and a second component contained in the liquid as well as a value equivalent to the temperature of the biosensor are calculated using a set of the first current value, the second current value, and the third current value generated when the first voltage and the second voltage, were applied, respectively.

A liquid sample measurement method according to a tenth aspect of the present invention is a liquid sample measurement method in which the amounts of components are measured using a biosensor in which a liquid is introduced and then components contained in said liquid are subjected to oxidation-reduction using an oxidoreductase, wherein the liquid sample measurement method includes: a first current value measurement step for detecting, as a first current value, an oxidation-reduction current that is generated by the oxidation-reduction when a first voltage is applied to a first electrode pair, which composes the biosensor; a second current value measurement step for detecting, as a second current value, a current that is generated when a second voltage is applied to a second electrode pair, which composes the biosensor and a third current value measurement, step for detecting, as a third current value, a current that is generated when a third voltage is applied to a third electrode pair, which composes the biosensor, a voltage value and a voltage application period of each of the first voltage, the second voltage, and the third voltage are controlled, each measurement timing for measuring the first current value, the second current value, and the third current value is controlled, and the amounts of a first component and a second component contained in the liquid as well as a value equivalent to the temperature of the biosensor are calculated using a set of the first current value, the second current value, and the third current value generated when the first voltage, the second voltage, and the third voltage were applied, respectively.

A liquid sample measurement method according to an eleventh aspect of the present invention is a liquid sample measurement method in which the amounts of components are measured using a biosensor in which a liquid is introduced and then components contained in said liquid are subjected to oxidation-reduction using an oxidoreductase, wherein the liquid sample measurement method includes: a temperature detection step for detecting ambient temperature; a first current value measurement step for detecting, as a first current value, an oxidation-reduction current that is generated by the oxidation-reduction when a first voltage is applied to a first electrode pair, which composes the biosensor; a second current value measurement step for detecting, as a second current value, a current that is generated when a second voltage is applied to a second electrode pair, which composes the biosensor; and a third current value measurement step for detecting, as a third current value, a current that is generated when a third voltage is applied to a third electrode pair, which composes the biosensor, a voltage value and a voltage application period of each of the first voltage, the second voltage, and the third voltage are controlled, each measurement timing for measuring the first current value, the second current value, and the third current value is controlled, the measurement timing is controlled so that a fourth current value that is different from the first current value and the second current value is measured in the first current value measurement step, the amounts of a first component and a second component contained in the liquid as well as a value equivalent to the temperature of the biosensor are calculated, and a step of said calculation includes: a first calculation step for calculating the amounts of the first component and the second component contained in the liquid as well as a first temperature equivalent value that is equivalent to the temperature of the biosensor using a set of the first current value, the second current value, and the fourth current value generated when the first voltage and the second voltage were applied, respectively; a second calculation step for calculating the amounts of the first component and the second component contained in the liquid as well as a second temperature equivalent value that is equivalent to the temperature of the biosensor using a set of the first current value, the second current value, and the third current value generated when the first voltage, the second voltage, and the third voltage were applied, respectively; and a recalculation step in which the amount of the first component is recalculated based on the amount of the first component calculated in the first calculation step and the amount of the first component calculated in the second calculation step, the amount of the second component is recalculated based on the amount of the second component calculated in the first calculation step and the amount of the second component calculated in the second calculation step and the temperature of the biosensor is recalculated based on the temperature detected in the temperature detection step, the fast temperature equivalent value, and the second temperature equivalent value.

A liquid sample measurement method according to a twelfth aspect of the present invention is the liquid sample measurement method of the above-mentioned ninth or tenth aspect, wherein the third current value is measured while the first voltage is applied to the first electrode pair.

A liquid sample measurement method according to a thirteenth aspect of the present invention is the liquid sample measurement method of the above-mentioned ninth or tenth aspect, wherein the third current value is measured after the second voltage is applied to the second electrode pair.

A liquid sample measurement method according to a fourteenth aspect of the present invention is the liquid sample measurement method of the above-mentioned ninth or tenth aspect, wherein recorded data containing the first current value, the second current value, and the third current value recorded per temperature and liquid containing the first component and the second component whose amounts are known is stored, the recorded data is compared with measured data containing the first current value that was measured, the second current value that was measured, and the third current value that was measured, and then the amount of the first component of the liquid from which the recorded data most approximated to said measured data was obtained is calculated as the amount of the first component of the liquid introduced into the biosensor.

A liquid sample measurement method according to a fifteenth aspect of the present invention is the liquid sample measurement method of the above-mentioned eleventh aspect, wherein first recorded data containing the first current value, the second current value, and the fourth current value recorded per temperature and liquid containing the first component and the second component whose amounts are known is stored, and in the first calculation step, the first recorded data is compared with measured data containing the first current value that was measured, the second current value that was measured, and the fourth current value that was measured, and then the amounts of the first component and the second component of the liquid from which the recorded data most approximated to said measured data was obtained as well as the temperature of the biosensor at which the recorded data most approximated to said measured data was obtained are calculated as the amounts of the first component and the second component of the liquid introduced into the biosensor and the first temperature equivalent value, and second recorded data containing the first current value, the second current value, and the third current value recorded per temperature and liquid containing the first component and the second component whose amounts are known is stored, and in the second calculation step, the second recorded data is compared with measured data containing the first current value that was measured, the second current value that was measured, and the third current value that was measured, and the amounts of the first component and the second component of the liquid from which the recorded data most approximated to said measured data was obtained as well as the temperature of the biosensor at which the recorded data most approximated to said measured data was obtained are calculated as the amounts of the first component and the second component of the liquid introduced into the biosensor and the second temperature equivalent value.

A biosensor according to a sixteenth aspect of the present invention is a biosensor in which a liquid is introduced and then liquid components contained in said liquid are subjected to oxidation-reduction using an oxidoreductase, wherein the biosensor includes: a first electrode pair including a first working electrode and a first counter electrode that contact the oxidoreductase and a mediator; a second electrode pair including a second working electrode, that does not contact the oxidoreductase or the mediator, and a second counter electrode that contacts the oxidoreductase and the mediator but does not contact the first working electrode of the first electrode pair; and a third electrode pair in which a third working electrode and a third counter electrode disposed at positions that do not contact the oxidoreductase or the mediator are provided and a voltage is applied, with said third working electrode being used as the second working electrode in the second electrode pair.

A liquid sample measurement device according to a seventeenth aspect of the present invention is a liquid sample measurement device that measures the amounts of components using a biosensor in which a liquid is introduced and then components contained in said liquid are subjected to oxidation-reduction using an oxidoreductase, wherein the liquid sample measurement device, includes:

a first current value measurement means that detects, as a first current value, an oxidation-reduction current that is generated by the oxidation-reduction when a first voltage is applied to a first electrode pair, which composes the biosensor;

a second current value measurement means that detects, as a second current value, a current that is generated when a second voltage is applied to a second electrode pair which composes the biosensor;

a third current value measurement means that detects, as a third current value, a current that is generated when a third voltage is applied to a third electrode pair, which composes the biosensor;

a control means that controls a voltage value and a voltage application period of each of the first voltage, the second voltage, and the third voltage, that applies the second voltage and the third voltage to the second electrode pair and the third electrode pair, respectively, while the first voltage is applied to the first electrode pair, and that controls each measurement timing for measuring the first current value, the second current value, and the third current value; and a calculation means that calculates the amounts of a first component and a second component contained in the liquid as well as a value equivalent to the temperature of the biosensor using a set of the first current value, the second current value, and the third current value generated when the first voltage, the second voltage, and the third voltage were applied, respectively.

A liquid sample measurement device according to an eighteenth aspect of the present invention is the liquid sample measurement device of the above-mentioned seventeenth aspect, wherein the liquid sample measurement device further includes a temperature detection means that detects ambient temperature, the first current measurement means further detects a fourth current value while the first voltage is applied to the first electrode pair, the control means further controls a measurement timing so as to measure the fourth current value at a timing different from those at which the first current value and the second current value are measured, the calculation means includes:

a first calculation means that calculates the amounts of a first component and a second component contained in the liquid as well as a first temperature equivalent value that is equivalent to the temperature of the biosensor using a set of the first current value, the second current value, and the fourth current value generated when the first voltage and the second voltage were applied, respectively; and a second calculation means that calculates the amounts of the first component and the second component contained in the liquid as well as a second temperature equivalent value that is equivalent to the temperature of the biosensor using a set of the first current value, the second current value, and the third current value generated when the first voltage, the second voltage, and the third voltage were applied, respectively, and the calculation means recalculates the amount of the first component based on the amount of the first component calculated by the first calculation means and the amount of the first component calculated by the second calculation means, recalculates the amount of the second component based on the amount of the second component calculated by the first calculation means and the amount of the second component calculated by the second calculation means, and recalculates the temperature of the biosensor based on the temperature detected by the temperature detection means as well as the first temperature equivalent value and the second temperature equivalent value.

A liquid sample measurement device according to a nineteenth aspect of the present invention is the liquid sample measurement device of the above-mentioned seventeenth or eighteenth aspect, wherein the control means exerts control so that while the first current value measurement means applies the first voltage to the first electrode pair, the third current value measurement means applies the third voltage to the third electrode pair to measure the third current value.

A liquid sample measurement device according to a twentieth aspect of the present invention is the liquid sample measurement device according to any one of the seventeenth to nineteenth aspects, wherein the control means exerts control so that after the second current value measurement means applies the second voltage to the second electrode pair, the third current value measurement means applies the third voltage to the third electrode pair to measure the third current value.

A liquid sample measurement device according to a twenty-first aspect of the present invention is the liquid sample measurement device according to any one of the above-mentioned seventeenth to twentieth aspects, wherein the liquid sample measurement device includes a storage means that contains recorded data stored therein in which per temperature and liquid containing the first component and the second component whose amounts are known, the first current value, the second current value, and the third current value obtained with respect to the liquid were recorded, and the calculation means compares the recorded data with measured data containing the first current value that was measured, the second current value that was measured, and the third current value that was measured, to calculate the amount of the first component of the liquid from which the recorded data most approximated to said measured data was obtained, as the amount of the first component of the liquid introduced into the biosensor.

A liquid sample measurement device according to a twenty-second aspect of the present invention is the liquid sample measurement device according to any one of the above-mentioned eighteenth to twenty-first aspects, wherein the liquid sample measurement device includes a first storage means that contains recorded data stored therein in which per temperature and liquid containing the first component and the second component whose amounts are known, the first current value, the second current value, and the fourth current value obtained with respect to the liquid were recorded, the first calculation means compares the recorded data with measured data containing the first current value that was measured, the second current value that was measured, and the fourth current value that was measured, to calculate the amounts of the first component and the second component of the liquid from which the recorded data most approximated to said measured data was obtained as well as the temperature of the biosensor at which the recorded data most approximated to said measured data was obtained, as the amounts of the first component and the second component of the liquid introduced into the biosensor and the first temperature equivalent value, the liquid sample measurement device includes a second storage means that contains recorded data stored therein in which per temperature and liquid containing the first component and the second component whose amounts are known, the first current value, the second current value, and the third current value obtained with respect to the liquid were recorded, and the second calculation means compares the recorded data with measured data containing the first current value that was measured, the second current value that was measured, and the third current value that was measured, to calculate the amounts of the first component and the second component of the liquid from which the recorded data most approximated to said measured data was obtained as well as the temperature of the biosensor at which the recorded data most approximated to said measured data was obtained, as the amounts of the first component and the second component of the liquid introduced into the biosensor and the second temperature equivalent value.

A liquid sample measurement device according to a twenty-third aspect of the present invention is the liquid sample measurement device according to any one of the above-mentioned seventeenth to twenty-second aspects, wherein the third electrode pair is composed of a first electrode that does not contact the oxidoreductase or a mediator and an electrode that does not contact the oxidoreductase or the mediator and that selected from the second electrode pair of the second current value measurement means.

A liquid sample measurement device according to a twenty-fourth aspect of the present invention is the liquid sample measurement device according to any one of the above-mentioned seventeenth to twenty-third aspects, wherein the third current value measurement means further detects, as a fourth current value, a current that is generated when a fourth voltage is applied to the third electrode pair, which composes the biosensor, at a timing different from that at which the third current value is detected, and the calculation means calculates the amounts of the first component and the second component contained in the liquid as well as the value equivalent to the temperature of the biosensor using the fourth current value in addition to the first current value, the second current value, and the third current value.

A liquid sample measurement device according to a twenty-fifth aspect of the present invention is the liquid sample measurement device according to any one of the above-mentioned seventeenth to twenty-fourth aspects, wherein the third current value measurement means further detects, as a fifth current value, a current that is generated when a fifth voltage is applied to the third electrode pair, which composes the biosensor, at a timing different from those at which the second current value and the third current value are detected, and the calculation mean calculates the amounts of the first component and the second component contained in the liquid as well as the value equivalent to the temperature of the biosensor using the fifth current value in addition to the first current value, the second current value, and the third current value.

A liquid sample measurement method according to a twenty-sixth aspect of the present invention is a liquid sample measurement method of measuring the amounts of components using a biosensor in which a liquid is introduced and then components contained in said liquid are subjected to oxidation-reduction using an oxidoreductase, wherein the liquid sample measurement method includes:

a first current value measurement step for detecting, as a first current value, an oxidation-reduction current that is generated by the oxidation-reduction when a first voltage is applied to a first electrode pair, which composes the biosensor;

a second current value measurement step for detecting, as a second current value, a current that is generated when a second voltage is applied to a second electrode pair, which composes the biosensor, while the first voltage is applied to the first electrode pair;

a third current value measurement step for detecting, as a third current value, a current that is generated when a third voltage is applied to a third electrode pair, which composes the biosensor, while the first voltage is applied to the first electrode pair; and a calculation step for calculating the amounts of a first component and a second component contained in the liquid as well as a value equivalent to the temperature of the biosensor using a set of the first current value, the second current value, and the third current value generated when the first voltage, the second voltage, and the third voltage were applied, respectively.

A liquid sample measurement method according to a twenty-seventh aspect of the present invention is the liquid sample measurement method of the above-mentioned twenty-sixth aspect, wherein the liquid sample measurement method further includes a temperature detection step for detecting an ambient temperature, and the calculation step includes:

a first calculation step for calculating the amounts of the first component and the second component contained in the liquid as well as a first temperature equivalent value that is equivalent to the temperature of the biosensor using a set of the first current value, the second current value, and the fourth current value generated when the first voltage and the second voltage were applied, respectively;

a second calculation step for calculating the amounts of the first component and the second component contained in the liquid as well as a second temperature equivalent value that is equivalent to the temperature of the biosensor using a set of the first current value, the second current value, and the third current value generated when the first voltage, the second voltage, and the third voltage were applied, respectively; and a recalculation step for recalculating the amount of the first component based on the amount of the first component calculated in the first calculation step and the amount of the first component calculated in the second calculation step, recalculating the amount of the second component based on the amount of the second component calculated in the first calculation step and the amount of the second component calculated in the second calculation step, and recalculating the temperature of the biosensor based on the temperature detected in the temperature detection step as well as the first temperature equivalent value and the second temperature equivalent value, A liquid sample measurement method according to a twenty-eighth aspect of the present invention is the liquid sample measurement method according to the above-mentioned twenty-sixth or twenty-seventh aspect, wherein the third current value measurement step includes measuring the third current value while the first voltage is applied to the first electrode pair.

A liquid sample measurement method according to a twenty-ninth aspect of the present invention is the liquid sample measurement method according to any one of the above-mentioned twenty-sixth to twenty-eighth aspects, wherein the third current, value measurement step includes measuring the third current value after the second voltage is applied to the second electrode pair.

A liquid sample measurement method according to a thirtieth aspect of the present invention is the liquid sample measurement method according to any one of the above-mentioned twenty-sixth to twenty-ninth aspects, wherein in the calculation step, recorded data, in which per temperature and liquid containing the first component and the second component whose amounts are known, the first current value, the second current value, and the third current value obtained with respect to the liquid were recorded, is compared with measured data containing the first current value that was measured, the second current value that was measured, and the third current value that was measured, and the amount of the first component of the liquid from which the recorded data most approximated to said measured data was obtained is calculated as the amount of the first component of the liquid introduced into the biosensor.

A liquid sample measurement method according to a thirty-first aspect of the present invention is the liquid sample measurement method according to any one of the above-mentioned twenty-seventh to thirtieth aspects, wherein the calculation step includes:

comparing first recorded data, in which per temperature and liquid containing the first component and the second component whose amounts are known, the first current value, the second current value, and the fourth current value obtained with respect to the liquid were recorded, with measured data containing the first current value that was measured, the second current value that was measured, and the fourth current value that was measured, to calculate the amounts of the first component and the second component of the liquid from which the recorded data most approximated to said measured data was obtained as well as the temperature of the biosensor at which the recorded data most approximated to said measured data was obtained, as the amounts of the first component and the second component of the liquid introduced into the biosensor and the first temperature equivalent, value, and comparing second recorded data, in which per temperature and liquid containing the first component and the second component hose amounts are known, the first current value, the second current value, and the third current value obtained with respect to the liquid were recorded, with measured data containing the first current value that was measured, the second current value that was measured, and the third current value that was measured, to calculate the amounts of the first component and the second component of the liquid from which the recorded data most approximated to said measured data was obtained as well as the temperature of the biosensor at which the recorded data most approximated to said measured data was obtained, as the amounts of the first component and the second component of the liquid introduced into the biosensor and the second temperature equivalent value.

A liquid sample measurement method according to a thirty-second aspect of the present invention is the liquid sample measurement method according to any one of the above-mentioned twenty-sixth to thirty-first aspects, wherein the liquid sample measurement method further includes a fourth current measurement step for detecting, as a fourth current value, a current that is generated when a fourth voltage is applied to the third electrode pair which composes the biosensor, at a timing different from that at which the third current value is detected, and in the calculation step, the amounts of the first component and the second component contained in the liquid as well as the value equivalent to the temperature of the biosensor are calculated using the fourth current value in addition to the first current value, the second current value, and the third current value.

A liquid sample measurement method according to a thirty-third aspect of the present invention is the liquid sample measurement method according to any one of the above-mentioned twenty-sixth to thirty-second aspects, wherein the liquid sample measurement method further includes a fifth current measurement step for detecting, as a fifth current value, a current that is generated when a fifth voltage is applied to the third electrode pair, which composes the biosensor, at a timing different from those at which the second current value and the third current value are detected, and in the calculation step, the amounts of the first component and the second component contained in the liquid as well as the value equivalent to the temperature of the biosensor are calculated using the fifth current value in addition to the first current value, the second current value, and the third current value.

Effects of the Invention

According to the present invention, voltage application in a biosensor is controlled to allow the amounts of the components of a liquid to be measured with a high accuracy.

BRIEF DESCRIPTION OF DRAWINGS

FIG. 9 is a table showing the electrodes, applied voltage, application timing, and application time in the voltage application pattern employed by the liquid sample measurement device shown as an embodiment of the present invention.

FIG. 10A shows the case where the first voltage was set at 350 mV, and FIG. 10B shows the case where the first voltage was set at 500 mV.

FIG. 12 is a table showing the electrodes, applied voltage, application timing, and application time in the voltage application pattern employed as the comparative example.

FIG. 15 is a table showing the electrodes, applied voltage, application timing, and application time in the voltage application pattern employed by the liquid sample measurement device shown as an embodiment of the present invention.

FIG. 29 is a table showing the electrodes, applied voltage, application timing, and application time in the voltage application pattern employed by the liquid sample measurement device shown as an embodiment of the present invention.

FIG. 32 is a table showing the electrodes, applied voltage, application timing, and application time in the voltage application pattern employed by the liquid sample measurement device shown as an embodiment of the present invention.

FIG. 35 is a table showing the electrodes, applied voltage, application timing, and application time in the voltage application pattern used as a comparative example.

DESCRIPTION OF THE INVENTION

Hereinafter, embodiments of the present invention are described with reference to the drawings.

First, a biosensor 1 is described.

Figure 1:
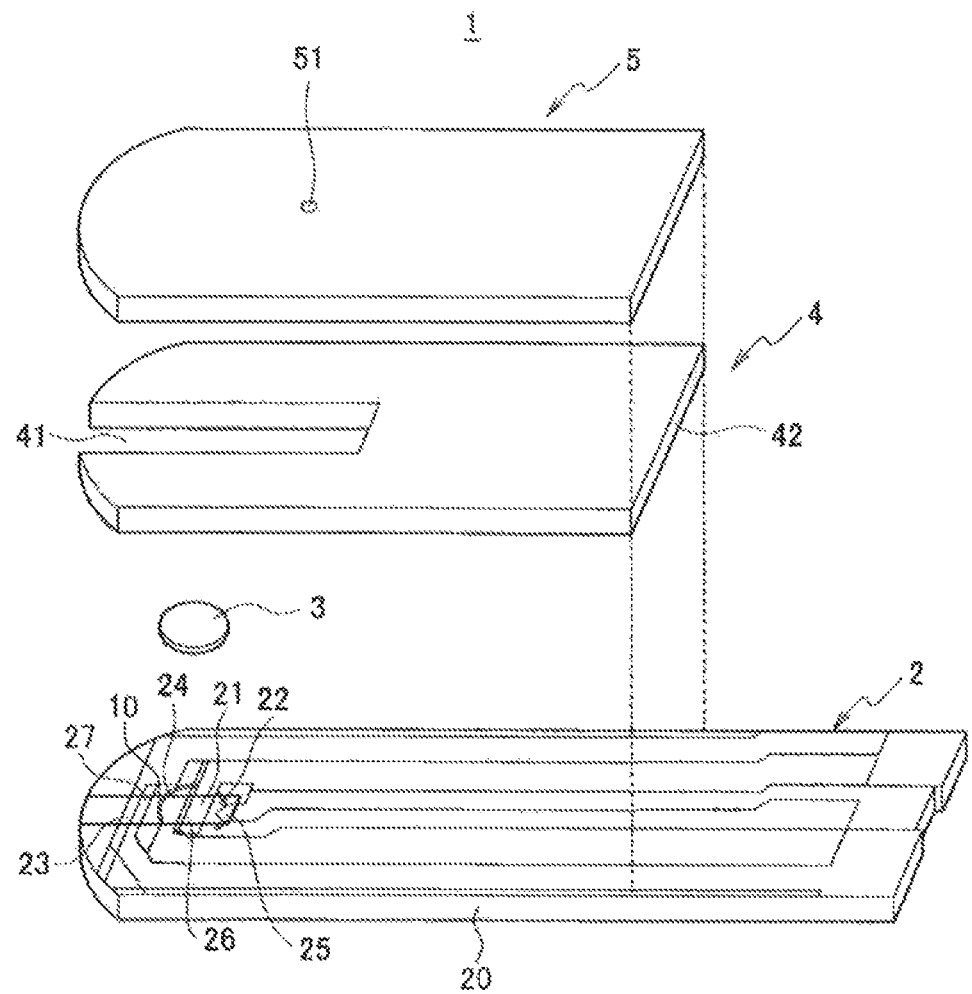
FIG. 1 is an exploded perspective view of a biosensor shown as an embodiment of the present invention.
Figure 2:
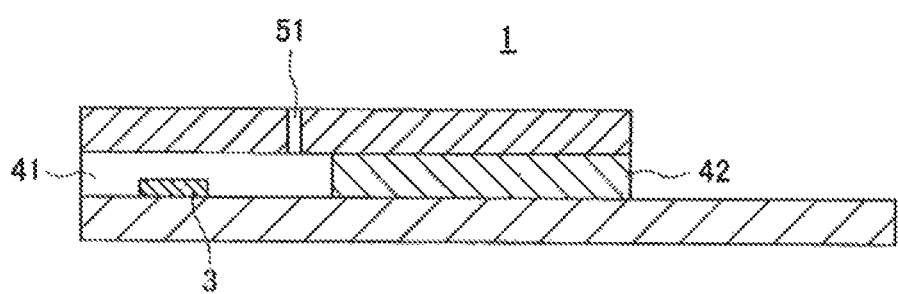
FIG. 2 is a cross-sectional view of the biosensor shown as an embodiment of the present invention.
Figure 3:
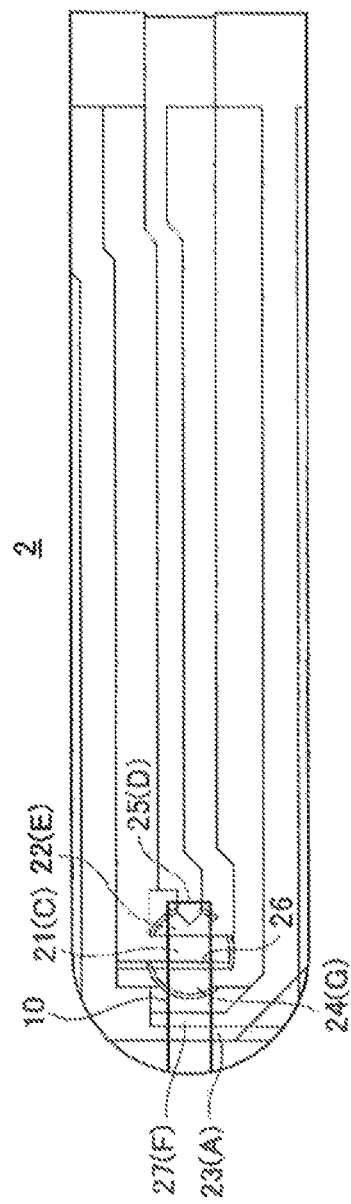
FIG. 3 is a top view of a blood component measurement layer of the biosensor shown as an embodiment of the present invention.

The biosensor 1 shown as an embodiment of the present invention includes, for example, such respective parts as shown in FIG. 1 or FIG. 3. FIG. 1 is an exploded perspective view of the biosensor 1. FIG. 2 is a cross-sectional view of the biosensor 1. The biosensor 1 includes a blood component measurement layer 2, a reagent layer 3, a spacer layer 4, and a surface layer 5. The biosensor 1 is formed of these respective layers stacked together. The biosensor 1 is described below using, as an example, a biosensor that measures glucose and blood cells as blood cell components but it is not limited thereto.

The biosensor 1 can be attached to or detached from a liquid sample measurement device 6 described later. The biosensor 1 composes a biosensor system together with the liquid sample measurement device 6. Using the liquid sample measurement device 6, the biosensor system measures the amounts of liquid components of the matrix contained in blood spotted as a sample to a sample spotting site 41 located at the tip of the biosensor 1. The liquid sample measurement device 6 displays, as measurement results, the amounts of blood components (the concentration of glucose (the amount of a first component) and the amount of blood cells (the amount of a second component)) that were measured.

In order to quantify the amounts of blood components in the blood using the biosensor 1, first an end of the biosensor 1 is inserted into the liquid sample measurement device 6 by a user. Then the liquid, sample measurement device 6 applies voltages to the electrodes of the biosensor 1 described later. In this state, blood is supplied to the sample spotting site 41. When the blood, is spotted, said blood is drawn into the biosensor 1. This blood dissolves the reagent layer 3. The liquid sample measurement device 6 detects the electrical change generated between the electrodes of the biosensor 1 to measure the amounts of blood components.

In the present embodiment, the biosensor 1 measures the amounts of specific blood components contained in the blood of a human body used as a sample liquid. The amounts of specific blood components include the concentration of glucose. In the following description, disclosure is made regarding the measurement of the concentration of glucose contained in the blood of a human body. However, the biosensor system in the present embodiment can also measure lactic acid, cholesterol, and other components when suitable enzymes are selected.

The blood component measurement layer 2 is configured with a conductive layer formed on an insulating substrate 20 that is formed of, for example, polyethylene terephthalate (PET), polycarbonate (PC), polyimide (PI), polyethylene (PE), polypropylene (PP), polystyrene (PS), polyvinyl chloride (PVC), polyoxymethylene (POM), monomer cast nylon (MC), polybutylene terephthalate (PBT), methacrylic resin (PMMA), ABS resin (ABS), or glass. The conductive layer is formed of an electroconductive material such as carbon or noble metal such as gold, platinum, or palladium, for example. The conductive layer is formed by for example, a screen printing method or a sputter deposition method. The conductive layer can be formed on the hole surface or at least a part of the substrate. The conductive layer may be coated with a polymeric material for the purpose of preventing impurities from adhering thereto or preventing it from being oxidized. The coating of the surface of the conductive layer can be carried out by, for example, preparing a solution of the polymeric material, dropping or applying it to the surface of the conductive layer, and then drying it. Examples of the drying method include natural drying, air drying, hot air drying, and heat drying.

Furthermore, the size of the insulating substrate 20 is not particularly limited. It has, for example, a total length of 5 to 100 mm, a width of 2 to 50 mm, and a thickness of 0.05 to 2 mm, preferably a total length of 7 to 50 mm, a width of 3 to 20 mm, and a thickness of 0.1 to 1 mm, and further preferably a total length of 10 to 30 mm, a width of 3 to 10 mm, and a thickness of 0.1 to 0.6 mm.

Moreover, the material of the spacer layer 4 is not particularly limited. For example, a similar material to that of the substrate 20 can be used. Furthermore, the size of the spacer layer 4 is not particularly limited. It has, for example, a total length of 5 to 1.00 mm, a width of 2 to 50 mm, and a thickness of 0.01 to 1 mm, preferably a total length of 7 to 50 mm, a width of 3 to 20 mm, and a thickness of 0.05 to 0.5 mm, and more preferably a total length of 10 to 30 mm a width of 3 to 10 mm, and a thickness of 0.05 to 0.25 mm. The spacer layer 4 has an I-shaped cutaway portion formed to serve as the sample spotting site 41 for introducing blood.

The surface layer 5 is an insulating substrate provided with an air hole 51 in the central portion thereof. The surface layer 5 is disposed to form one body together with the blood component measurement layer 2, with the spacer layer 4 having the sample spotting site 41 as a cutaway portion being interposed between the surface layer 5 and the blood component measurement layer 2. In order to form one body, the surface layer 5, the spacer layer 4, and the blood component measurement layer 2 may be bonded together with an adhesive or may be heat-sealed. Examples of the adhesive that can be used herein include an epoxy adhesive, an acrylic adhesive, a polyurethane adhesive, as well as to thermosetting adhesive (such as a hot-melt adhesive) and a UV curable adhesive.

The material of the surface layer 5 is not particularly limited but, for example, a similar material to that of the substrate 20 can be used. It is further preferable that the portion corresponding to the ceiling portion of the sample spotting site 41 of the surface layer 5 be subjected to a hydrophilic treatment. Examples of the method used for the hydrophilic treatment include a method in which a surfactant is applied and a method in which a hydrophilic functional group such as a hydroxyl group, a carbonyl group, or a carboxyl group is introduced into the surface of the surface layer 5 by, for example, a plasma treatment. The size of the surface layer 5 is not particularly limited but it has, for example, a total length of 5 to 100 mm, a width of 3 to 50 mm, and a thickness of 0.01 to 0.5 mm, preferably a total length of 10 to 50 mm, a width of 3 to 20 mm, a thickness of 0.05 to 0.25 mm, and more preferably a total length of 15 to 30 mm, a width of 5 to 10 mm, and a thickness of 0.05 to 0.1 mm. Preferably, the air hole 51 is formed in the surface layer 5. The shape thereof is, for example, round, oval, or polygonal. The air hole 51 has, for example, a maximum diameter of 0.01 to 10 mm, preferably a maximum diameter of 0.05 to 5 mm, and more preferably a maximum diameter of 0.1 to 2 mm.

In the blood component measurement layer 2, as shown in FIG. 3, a plurality of slits are provided for the conductive layer located on the substrate 20 to form various electrodes. FIG. 3 is a top view of the blood component measurement layer 2 in the biosensor 1. In the blood component measurement layer 2, a first electrode pair composed of a first working electrode 21(C) and a first counter electrode 22(E) is formed. The first working electrode 21 and the first counter electrode 22 are disposed at positions that contact an oxidoreductase and mediator of the reagent layer 3 described later. In the blood component measurement layer 2, a second electrode pair composed of a second working electrode 23(A) and a second counter electrode 24(G) is formed. The second working electrode 23 is disposed at a position that does not contact the oxidoreductase and mediator of the reagent layer 3 described later. The second counter electrode 24 is disposed at a position that contacts the oxidoreductase and mediator of the reagent layer 3 described later but does not contact the first working electrode 21. Furthermore, in the blood component measurement layer 2, a detection electrode 25 for detecting the introduction of blood is formed. These first working electrode 21, first counter electrode 22, second working electrode 23, second counter electrode 24, and detection electrode 25 are electrically connected to the liquid sample measurement device 6, with the biosensor 1 being inserted in the liquid sample measurement device 6.

When a first current value that depends on the concentration of glucose to a high degree is to be measured, a voltage (a first voltage) is applied between the first, working electrode 21 and the first counter electrode 22, with the first working electrode 21 and the first counter electrode 22 being used as a positive electrode and a negative electrode, respectively.

When a second current value that depends on the amount of blood cells to a high degree is to be measured, a voltage (a second voltage) is applied in the form of pulses between the second working electrode 23 and the second counter electrode 24, with the second working electrode 23 and the second counter electrode 24 being used as the positive electrode and the negative electrode, respectively. Examples of the form of pulses include forms of a rectangular wave, a triangular wave, etc. The details of such voltage applications are described later.

A non-interference portion 26 with no conductive layer formed thereon is provided between the first working electrode 21 and the second counter electrode 24. The non-interference portion 26 separates the first working electrode 21 and the second counter electrode 24 from each other. This allows the non-interference portion 26 to prevent the mediator generated in the second counter electrode 24 from flowing into the first working electrode 21 in measuring the second current value.

Furthermore, the blood component measurement layer 2 has a third electrode pair formed therein. In the present embodiment, the third electrode pair is composed of the second working electrode 23 (A, a third working electrode) and a third counter electrode 27 (F, a third counter electrode). When a third current value that depends on the temperature of the biosensor 1 to a high degree is to be measured, a voltage (a third voltage) is applied between the second working electrode 23 and the third counter electrode 27 with the second working electrode 23 and the third counter electrode 27 being used as the positive electrode and the negative electrode, respectively. In this case, the position of the third counter electrode 27 is not limited to the blood introduction side (the left-hand side in FIG. 3) in the biosensor 1. It may be positioned on the detection electrode 25 side (the right-hand side in FIG. 3; excluding the portion where the reagent layer 3 is located).

In the blood component measurement layer 2, an identification section for identifying the biosensor 1 using the liquid sample measurement device 6 may be formed with electrodes. The identification section has, for example, a shape for identifying the type of the biosensor 1 and the difference in output characteristics per production lot. The identification section is formed, for example, on the side of the end of the biosensor 1 and can be read by the liquid sample measurement device 6.

As shown in FIG. 1, the spacer layer 4 is disposed to cover the respective electrodes 21 to 24, 26, and 27 located on the substrate 20 of the blood component measurement layer 2. The spacer layer 4 is a substrate 42 in which the rectangular sample spotting site 41 provided at the front edge center is formed. The sample spotting site 41 forms a sample supply path 10 shown in FIG. 3. When blood is spotted on the sample spotting site 41, the blood is drawn towards the air hole 51 of the surface layer 5 to the right in FIGS. 1 to 3 by the capillary phenomenon. Thus, the blood is introduced into the first working electrode 21, the first counter electrode 22, and the second counter electrode 24.

As shown in FIG. 1, the reagent layer 3 is disposed between the blood component measurement layer 2 and the spacer layer 4. The reagent layer 3 is formed through application of a reagent containing, for example, an enzyme, a mediator (an electron acceptor), an amino acid, and sugar alcohol. The reagent layer 3 contacts the first working electrode 21 and the first counter electrode 22 that are exposed through the sample spotting site 41 of the spacer layer 4. Furthermore, the reagent layer 3 selectively contains, as optional components, a polymeric material, an enzyme stabilizer, a crystal homogenizer, etc. Over the blood component measurement layer 2 and the reagent layer 3, the surface layer 5 is disposed while leaving one end of the blood, component measurement layer 2 exposed, with the spacer layer 4 being interposed therebetween.

Examples of the oxidoreductase of the reagent layer 3 to be used herein include glucose oxidase, lactate oxidase, cholesterol oxidase, cholesterol esterase, uricase, ascorbate oxidase, bilirubin oxidase, glucose dehydrogenase, lactate dehydrogenase, and lactate dehydrogenase. The amount of the oxidoreductase is, for example, 0.01 to 100 U, preferably 0.05 to 10 U, and more preferably 0.1 to 5 U, per biosensor or per measurement. Among them, the oxidoreductase is preferably glucose oxidase or glucose dehydrogenase.

The mediator (the electron acceptor) of the reagent layer 3 is preferably ferricyanide, more preferably potassium ferricyanide. Examples of mediators other than the potassium ferricyanide that can be used herein include p-benzoquinone and derivatives thereof, phenazine methosulfate, methylene blue, as we as ferrocene and derivatives thereof.

For example, in order to measure the concentration of glucose (a blood component) in the blood of a human body, the biosensor 1 of the present embodiment uses glucose oxidase as an oxidoreductase and potassium ferricyanide as a mediator that are carried by the reagent layer 3.

In the reagent layer 3, when blood is introduced into the sample supply path 10, the oxidoreductase and the mediator are dissolved in the blood used as a sample liquid. Then, an enzyme reaction proceeds between them and the glucose, which is a matrix in the blood, and thereby the mediator is reduced to produce ferrocyanide (potassium ferrocyanide in the case of the present embodiment). After completion of this reaction, the mediator thus reduced is electrochemically oxidized, and from the current obtained thereby, a response value (a first response value (mV)) that depends on the concentration of glucose in the blood to a high degree is measured.

In the present invention, the blood cells denote red blood cells, white blood cells, platelets, and combinations thereof, which are contained in the blood, but preferably the blood cells denote red blood cells. Furthermore, in the present invention, the amount of the blood cells denotes, for example, the ratio (volume ratio) of the red blood cells contained in the blood, preferably the hematocrit (Hct) value.

Next, the configuration of the liquid sample measurement device 6 is described.

The liquid sample measurement device 6 carries out measurement using the biosensor 1 in which blood is introduced and blood components contained in said blood are subjected to oxidation-reduction using the oxidoreductase. The liquid sample measurement device 6 measures the concentration of glucose and the amount of blood cells as the amounts of blood components and measures a temperature equivalent value that is a value equivalent to the temperature of the biosensor 1.

Figure 4:
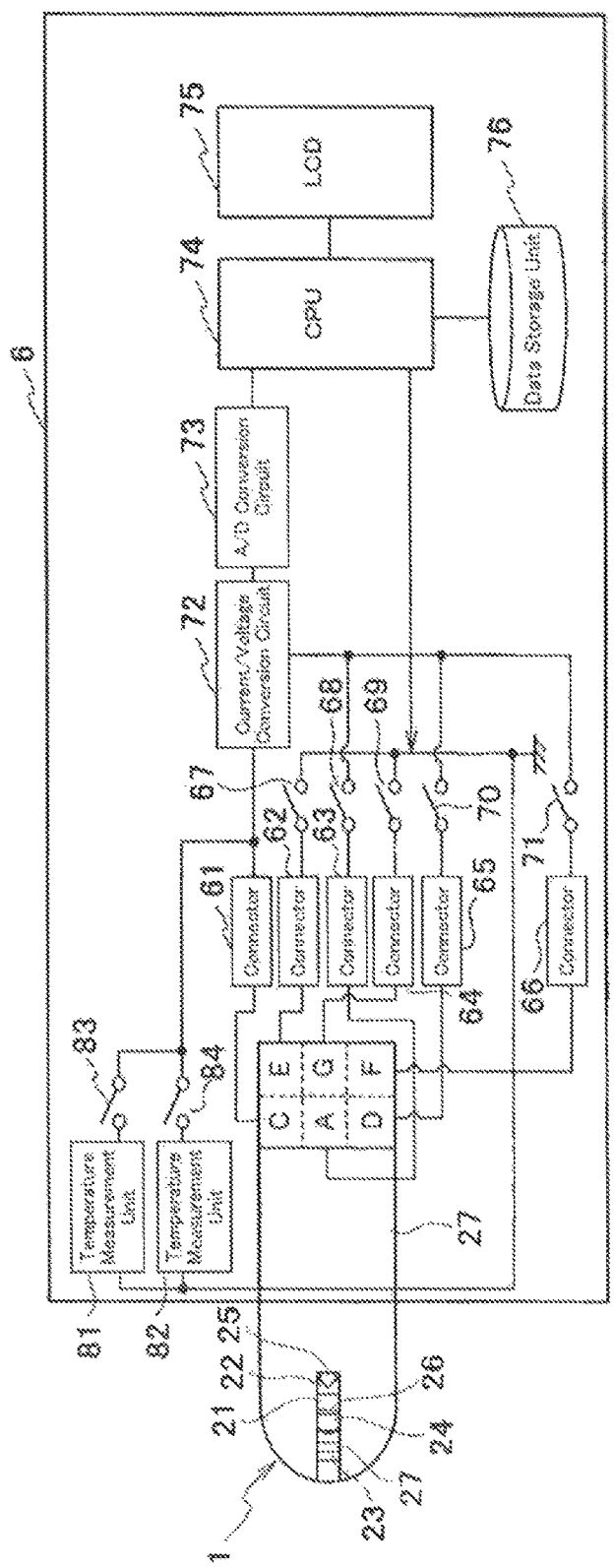
FIG. 4 is a block diagram showing the configuration of a measurement device shown as an embodiment of the present invention.

As shown in FIG. 4, the liquid sample measurement device 6 is connected to the electrodes A to F provided at the end of the biosensor 1, with the biosensor 1 being inserted in the liquid sample measurement device 6. The electrode C corresponds to the first working electrode 21, the electrode E corresponds to the first counter electrode 22, the electrode A corresponds to the second working electrode 23, the electrode corresponds to the second counter electrode 24, the electrode D corresponds to the detection electrode 25, and the electrode F corresponds to the third counter electrode 27.

The liquid sample measurement device 6 includes a plurality of connectors 61 to 66 and switches 67 to 71, a current/voltage conversion circuit 72, an A/D conversion circuit 73, a CPU 74, an LCD 75, and a data storage unit 76 (a storage means). Furthermore, the liquid sample measurement device 6 includes temperature measurement units 81, 82 (temperature detection means) for measuring the device inner temperature and switches 83, 84 for said temperature measurement units 81, 82. The connectors 62, 64 and the switches 67, 68 connected to the first counter electrode 22 and the second counter electrode 24 to serve, as negative electrodes are grounded.

The temperature measurement unit 81 and the temperature measurement unit 82 each measure the temperature inside the liquid sample measurement device 6 as the ambient temperature of the blood introduced. It is desirable that the temperature measurement units 81, 82 each measure the temperature of, for example, a position near the biosensor 1 inserted into the liquid sample measurement device 6. The temperature measurement values measured by the temperature measurement units 81, 82 are supplied to the CPU 74. The CPU 74 compares the two temperature measurement results. When the difference between the temperatures is not within a predetermined threshold, it is determined that one of the temperature measurement units 81, 82 is not working. This allows the failure of the liquid sample measurement device 6 to be detected accurately and easily. Furthermore, measurement errors caused by irregular temperature measurements are avoided. The temperature measurement timing may be immediately after the introduction of blood is detected by the detection electrode 25 or when the temperature of the blood introduced into the biosensor 1 is stabilized.

The liquid sample measurement device 6 does not have to be provided with the temperature measurement units 81, 82. The liquid sample measurement device 6 needs to be provided with the temperature measurement units 81, 82 only when a measured temperature is used in addition to the temperature equivalent value described later.

The respective connectors 61 to 66 are connected to the respective electrodes A and C to G of the biosensor 1. The respective switches 67 to 71 are connected to the connectors 62 to 66, respectively. The on/off states of the switches 67 to 71 are controlled by the CPU 74. When the first current value is to be measured, the switch 67 is turned on to apply a voltage between the electrode C connected to the first working electrode 21 and the electrode E connected to the first counter electrode 22. When the second current value is to be measured, the switches 68, 69 are turned on to apply a voltage between the electrode A connected to the second working electrode 23 and the electrode G connected to the second counter electrode 24. The voltage to be applied between the first working electrode 21 and the first counter electrode 22 as well as the voltage to be applied between the second working electrode 23 and the second counter electrode 24 can be changed. When the introduction of blood is to be detected, the switch 70 is turned on to apply a voltage to the electrode D connected to the detection electrode 23. When the third current value is to be measured, the switches 68, 71 are turned on to apply a voltage between the electrode A connected to the second working electrode 23 and the electrode F connected to the third counter electrode 27.

The current/voltage conversion circuit 72 is connected to the connectors 61 to 66 and the temperature measurement units 81, 82. The currents flowing between the first working electrode 21, the second working electrode 23, and the other electrodes are supplied to the current/voltage conversion circuit 72. Furthermore, currents corresponding to the ambient temperatures measured by the temperature measurement units 81, 82, are supplied to the current/voltage conversion circuit 72. The current/voltage conversion circuit 72 converts the currents thus supplied to voltages. The converted voltage values are supplied to the conversion circuit 73.

The A/D conversion circuit 73 is supplied with voltage values from the current/voltage conversion circuit 72. The A/D conversion circuit 73 converts the voltage values thus supplied to pulsed digital data and then outputs them to the CPU 74.

The CPU 74 controls respective parts included in the liquid sample measurement device 6. The CPU 74 exerts control for turning the respective switches 67 to 71 on or off in measuring the concentration of glucose, the amount of blood cells, and the temperature equivalent value. Furthermore, the CPU 74 controls voltage values that are applied to the respective electrode pairs (a control means).

Particularly, the CPU 74 controls the voltage value and voltage application period of each of the first voltage, the second voltage, and the third voltage. Moreover, the CPU 74 controls each measurement timing for measuring the first current value, the second current value, and the third current value.

Furthermore, the CPU 74 calculates the first response value (mV) equivalent to the first current value, the second response value (mV) equivalent to the second current value, and the third response value (mV) equivalent to the third current value based on the digital data supplied from the A/D conversion circuit 73. The CPU 74 converts the first response value, the second response value, and the third response value thus calculated to the concentration of glucose, the amount of blood cells, and the value equivalent to the temperature of the biosensor 1. In this case, the CPU 74 obtains the concentration of glucose, the amount of blood cells, and the value equivalent to the temperature of the biosensor 1 based on the first response value, the second response value, and the third response value obtained with respect to the blood in which the concentration of glucose and the amount of blood cells as well as the temperature of the biosensor 1 are known. The process for obtaining the concentration of glucose, the amount of blood cells, and the value equivalent to the temperature of the biosensor 1 from the first response value, the second response value, and the third response value is described later.

The LCD 75 is an LCD (a liquid crystal display; an output unit) that displays the measurement values calculated by the CPU 74.

The data storage unit 76 contains data stored therein that can be referred to by the CPU 74. The data storage unit 76 contains recorded data stored therein that are used for calculating the concentration of glucose by the CPU 74. The recorded data is composed of a first response value, a second response value, and a third response value included therein that are equivalent to the first current value, the second current value, and the third current value measured per temperature and blood in which the concentration of glucose and the value of the amount of blood cells are known.

Next, basic operations of the above-mentioned liquid sample measurement device 6 are described.

In the liquid sample measurement device 6, when the concentration of glucose, the amount of blood cells, and the value equivalent to the temperature of the biosensor 1 are to be measured, first the introduction of blood is detected by the detection electrode 25.

When obtaining the first current value to measure the first response value, the liquid sample measurement device 6 allows the CPU 74 to turn on the switch 67 to apply a voltage (the first voltage) between the first working electrode 21 and the first counter electrode 22 (the first electrode pair). In this state, the CPU 74 detects the oxidation-reduction current (the first response value) that is generated by oxidation-reduction (a first current value measurement means). The process for converting the first response value is described later.

When obtaining the second current value to measure the second response value, the liquid sample measurement device 6 allows the CPU 74 to turn on the switches 68, 69 to apply a voltage (the second voltage) between the second working electrode 23 and the second counter electrode 24 (the second electrode pair). In this state, the CPU 74 detects the second current value that is generated when the voltage is applied to the second working electrode 23 and the second counter electrode 24 (a second current value measurement means).

When obtaining the third current value to measure the third response value, the liquid sample measurement device 6 applies a voltage between the second working electrode 23 and the third counter electrode 27 of the third electrode pair to obtain the third current value (a third current value measurement means).

The CPU 74 calculates the amount of a first component, the amount of a second component, and the value equivalent to the temperature of the biosensor 1 that were measured, based on the first response value, the second response value, and the third response value that were measured (a calculation means). In this process, the CPU 74 refers to the recorded data. The CPU 74 compares a plurality of recorded data each containing the first response value, the second response value, and the third response value stored in the data storage unit 76 with the measured data containing the first response value, the second response value, and the third response value that were measured. The CPU 74 calculates the amount of the first component of the blood from which the recorded data most approximated to the measured data was obtained, as the amount of the first component (the concentration of glucose) of the blood introduced into the biosensor 1. Similarly, the CPU 74 calculates the amount of the second component of the blood from which the recorded data most approximated to the measured data was obtained, as the amount of the second component (the amount of blood cells) of the blood introduced into the biosensor 1. The CPU 74 calculates the value equivalent to the temperature of the biosensor 1 at which the recorded data most approximated to the measured data was obtained, as the value equivalent to the temperature of the biosensor 1 obtained at the time of measurement.

Next, the first response value, the second response value, and the third response value are described with respect to the operations for obtaining the amount of the first component, the amount of the second component, and the value equivalent to the temperature of the biosensor 1 in the liquid sample measurement device 6 as described above.

Figures 5, 6:
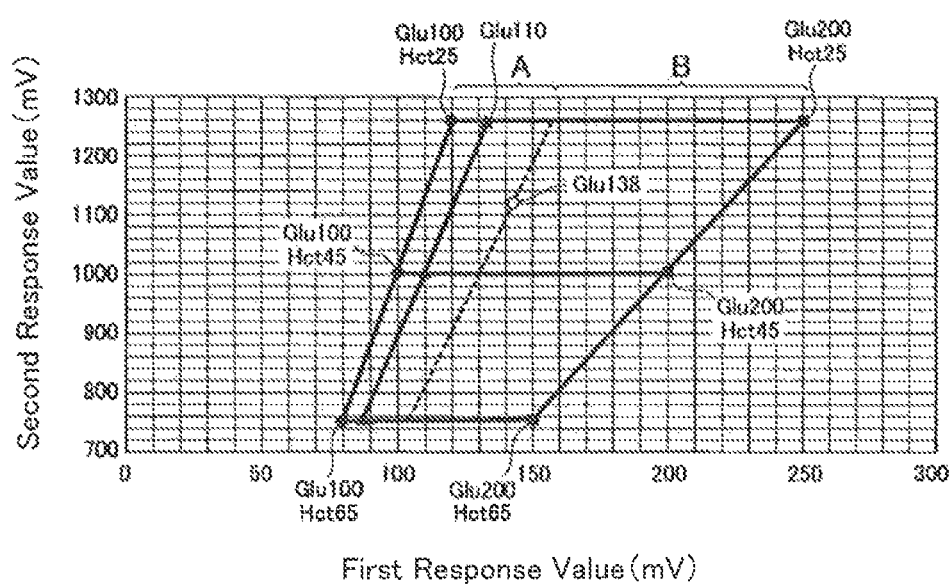
FIG. 5 is a table showing first response values and second response values with respect to known concentrations of glucose and amounts of blood cells.
FIG. 6 is a graph showing the relationship between the first response value and the second response value.

In the liquid sample measurement device 6, the first response value of the liquid sample measurement device 6 that is expected to be supplied to the CPU 74 is, for example, as shown in FIG. 5. For example, when the concentration of glucose is 100 mg/dl and the amount of blood cells (Hct) is 25% ("Hct25" in FIG. 5), the CPU 74 is expected to obtain a first response value of 120 as a current value and a second response value of 1250 as a current value. Such expected values of the first response value and the second response value can be obtained by preparing blood in which the concentration of glucose and the amount of blood cells have been regulated beforehand, and then carrying out measurement with the biosensor 1 and the liquid sample measurement device 6.

When the first response values and the second response values obtained from blood in which the concentration of glucose and the amount of blood cells are known, as shown in FIG. 5, are plotted and lines connecting the points thus plotted are drawn, a conversion matrix as shown in FIG. 6 can be created. This conversion matrix shows that the first response value changes when bloods have different amounts of blood cells even when having the same concentration of glucose.

In the conversion matrix, the first response values and the second response values that are plotted on the line connecting the points obtained at each known same concentration of glucose can be converted into said known concentration of glucose and amount of blood cells. Therefore, using the conversion matrix, the concentration of glucose and the amount of blood cells can be obtained from the first response value and the second response value obtained from unknown blood. For example, when the first response value and the second response value indicated with a white circle in FIG. 6 were obtained, the ratio (A:B) between the respective first response values at concentrations of glucose of 100 mg/dl and 200 mg/dl in the conversion matrix is taken. Conversion is made from this ratio and thereby a concentration of glucose of 138 mg/dl can be obtained in the blood from which the first response value and the second response value indicated with the white circle in FIG. 6 were obtained. Similarly, the ratio between the respective second response values at amounts of blood cells (Hct) of 25% and 65% in the conversion matrix is taken, and then the unknown amount of blood cells in the blood from which the first response value and the second response value indicated with the white circle in FIG. 6 were obtained can be determined.

As described above, preparing the conversion matrix allows the concentration of glucose and the amount of blood cells to be converted from the first response value and the second response value. Furthermore, the conversion matrix can include the third response value as described later. In this case, when the first response value, the second response value, and the third response value are obtained from blood using the liquid sample measurement device 6, the concentration of glucose, the amount of blood cells, and the value equivalent to the temperature of the biosensor 1 of the blood can be obtained.

Next, the process for determining the concentration of glucose and the amount of blood cells of the blood as well as the value equivalent to the temperature of the biosensor 1 by the above-mentioned liquid sample measurement device 6 is described.

Figure 7:
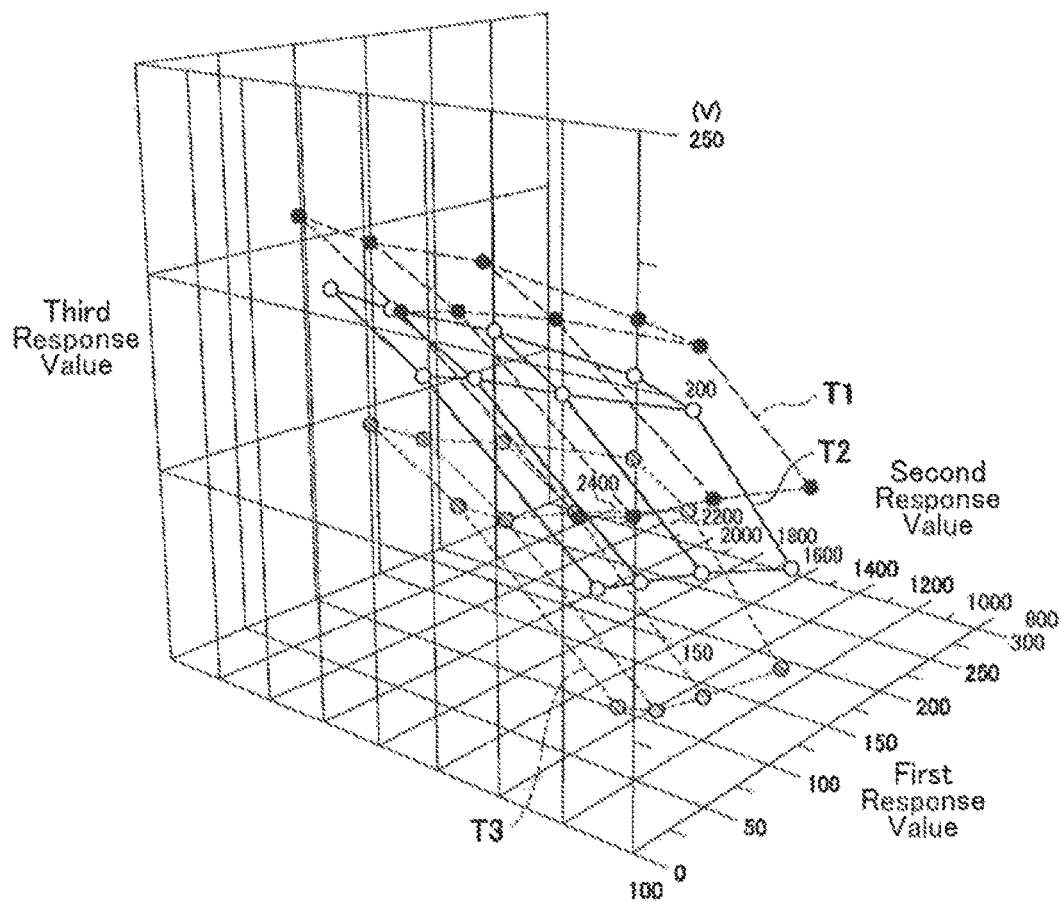
FIG. 7 is a graph showing conversion matrices illustrating the relationship between the first response value, the second response value, and the third response value.

As described above, the liquid sample measurement device 6 measures the first response value, the second response value, and the third response value of the blood. The relationship between the first response value, the second response value, and the third response value is, for example, as shown in FIG. 7. FIG. 7 shows conversion matrices illustrating the relationship between the first response value (mV), the second response value (mV), and the third response value (mV), per temperature T1, T2, T3 (° C.) of the biosensor 1.

With the temperature (° C.) of the biosensor 1 being known beforehand, using blood in which the concentration of glucose and the amount of blood cells were known, the first response value, the second response value, and the third response value were obtained by the liquid sample measurement device 6 to create the conversion matrices shown in FIG. 7. In the present embodiment, as an example, T1 is 20° C., T2 is 25° C., and T3 is 30° C.

According to FIG. 7, even if the temperature of the biosensor 1 is changed to T1, T2, or T3, a plurality of conversion matrices do not cross one another. That is, when the first response value, the second response value, and the third response value can be measured using blood in which the concentration of glucose and the amount of blood cells are unknown, the concentration of glucose, the amount of blood cells, and the value equivalent to the temperature of the biosensor 1 can be uniquely obtained by the liquid sample measurement device 6. On the other hand, when the planes formed by connecting the respective points forming the conversion matrices cross one another, a unique concentration of glucose, amount of blood cells, and value equivalent to the temperature of the biosensor 1 cannot be obtained by the liquid sample measurement device 6.

The liquid sample measurement device 6 stores, per temperature T1, T2, and T3 (° C.) of the biosensor 1, recorded data (conversion matrices) including the first response value, the second response value, and the third response value obtained using blood in which the concentration of glucose and the amount of blood cells are known, as shown in FIG. 7.

In order to obtain such conversion matrices, the liquid sample measurement device 6 controls the first voltage to be applied between the first working electrode 21 and the first counter electrode 22 as well as the application time. In addition, the liquid sample measurement device 6 controls the second voltage to be applied between the second working electrode 23 and the second counter electrode 24 as well as the application time. Furthermore, the liquid sample measurement device 6 applies the third voltage to be applied between the second working electrode 23 and the third counter electrode 27 as well as the application time. Moreover, the liquid sample measurement device 6 controls each measurement timing for measuring the first response value, the second response value, and the third response value. A means for exerting such controls is also referred to as a control means.

In the actual measurement of unknown blood, the first voltage, the second voltage, and the third voltage, are applied, respectively, in the same manner as when conversion matrices that do not cross one another were obtained as shown in FIG. 7 to measure the first response value, the second response value, and the third response value, respectively. The conversion matrices shown in FIG. 7 are compared with the first response value, second response value, and third response value that were measured and thereby a conversion matrix including the first response value, second response value, and third response value closest to the measured data is obtained. Thus, the liquid sample measurement device 6 can calculate the concentration of glucose, the amount of blood cells, and the temperature of the biosensor 1 at which said conversion matrix was obtained, as the concentration of glucose and the amount of blood cells of the unknown blood as well as the temperature of the biosensor 1.

Figure 8:
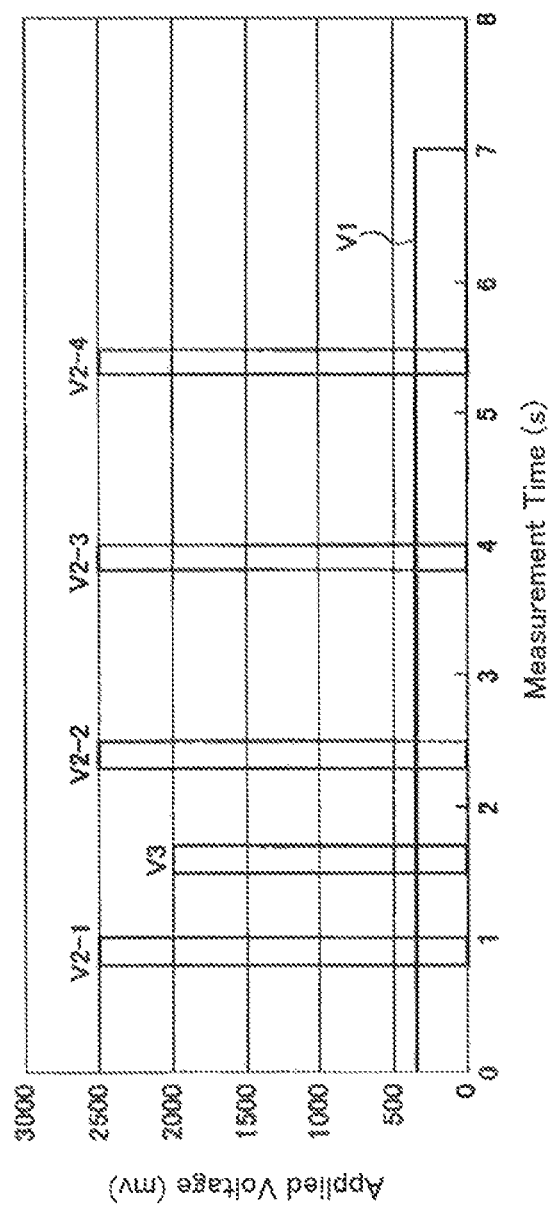
FIG. 8 is a graph showing the temporal change in voltage value in a voltage application pattern employed by a liquid sample measurement device shown as an embodiment of the present invention.

For example, as shown in FIG. 8, the liquid sample measurement device 6 controls the voltage values and application times of the first voltage, the second voltage, and the third voltage. The liquid sample measurement device 6 starts measuring current after a liquid to be measured is introduced into the biosensor 1 and then is detected by the detection electrode 25. The liquid sample measurement device 6 applies the first voltage V1 from the start to the end of measurement. Furthermore, the liquid sample measurement device 6 applies the second voltages V2-1, V2-2, V2-3, and V2-4 in the form of pulses for a plurality of times. Moreover, the liquid sample measurement device 6 applies the third voltage V3 after the first second voltage V2-1 but before the second voltage V2-2. When a plurality of second voltages are collectively referred to, they are referred to simply as the "second voltage V2".

The liquid sample measurement device 6 changes the electrode to which a voltage is applied, the applied voltage, the application time, and the application timing as shown in FIG. 9. The first voltage V1 is applied between the first working electrode 21(C) and the first counter electrode 22(E). The first voltage V1 is about 350 mV.

Each second voltage V2 is applied between the second working electrode 23(A) and the second counter electrode 24(G). Each second voltage V2 is about 2500 mV. The application time of each second voltage V2 is about 0.2 second.

The third voltage V3 is applied between the second working electrode 23(A) and the third counter electrode 27(F). The third voltage V3 is about 2000 mV. The application time of the third voltage V3 is 0.2 second.

The first voltage V1, second voltage V2, and third voltage V3 whose applied voltage, application timing, and application time are as described above each are applied and thereby the liquid sample measurement device 6 obtains the first response value, the second response value, and the third response value with respect to the blood. When the operation for obtaining the first response value, the second response value, and the third response value is carried out, at known temperatures, with respect to the blood in which the concentration of glucose and the amount of blood cells are known, the liquid sample measurement device 6 can obtain such conversion matrices as shown in FIG. 7. For example, when blood in which the concentration of glucose and the amount of blood cells are unknown is introduced into the biosensor 1, the liquid sample measurement device 6 applies the first voltage V1, the second voltage V2, and the third voltage V3 as shown in FIGS. 8 and 9. The liquid sample measurement device 6 thereby can obtain the first response value, the second response value, and the third response value with respect to the unknown blood. Finally, using the conversion matrices, the liquid sample measurement device 6 can uniquely obtain the glucose conversion value, the blood cell amount conversion value, and the value equivalent to the temperature of the biosensor 1 from the first response value, the second response value, and the third response value obtained with respect to the unknown blood.

Figure 10A:
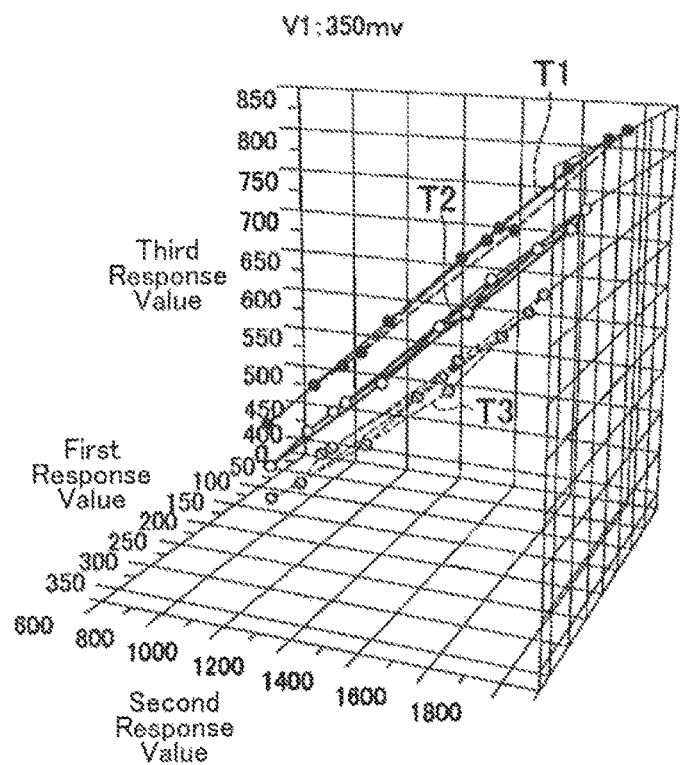
FIGS. 10A and 10B each are a graph showing conversion matrices illustrating the relationship between the first response value, the second response value, and the third response value.
Figure 10B:
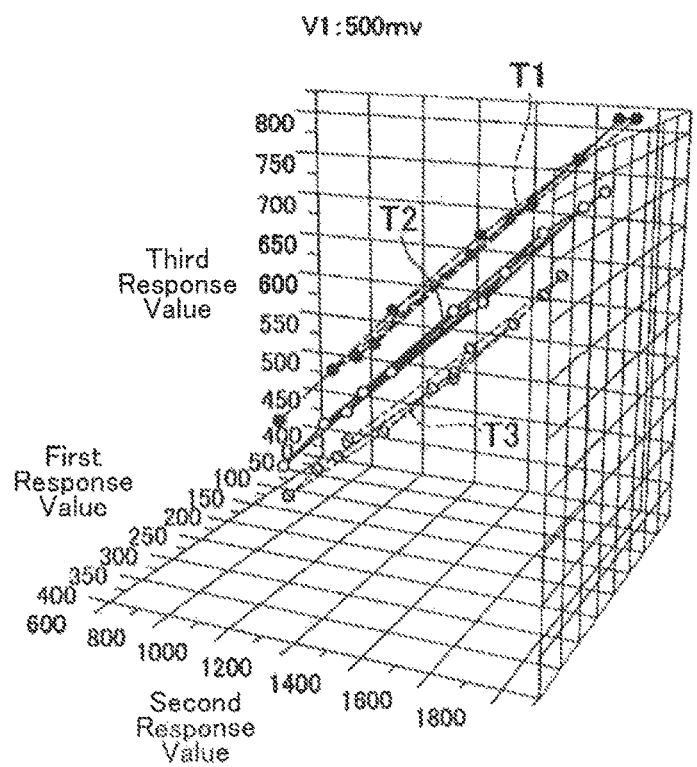

As shown in FIG. 10, according to the liquid sample measurement device 6 of the present invention, even when the voltage value of the first voltage V1 is changed, conversion matrices that do not cross one another can be obtained. FIG. 10A shows conversion matrices obtained when the first voltage V1 was set at 350 mV. FIG. 10B shows conversion matrices obtained when the first voltage V1 was set at 500 mV.

Figure 11:
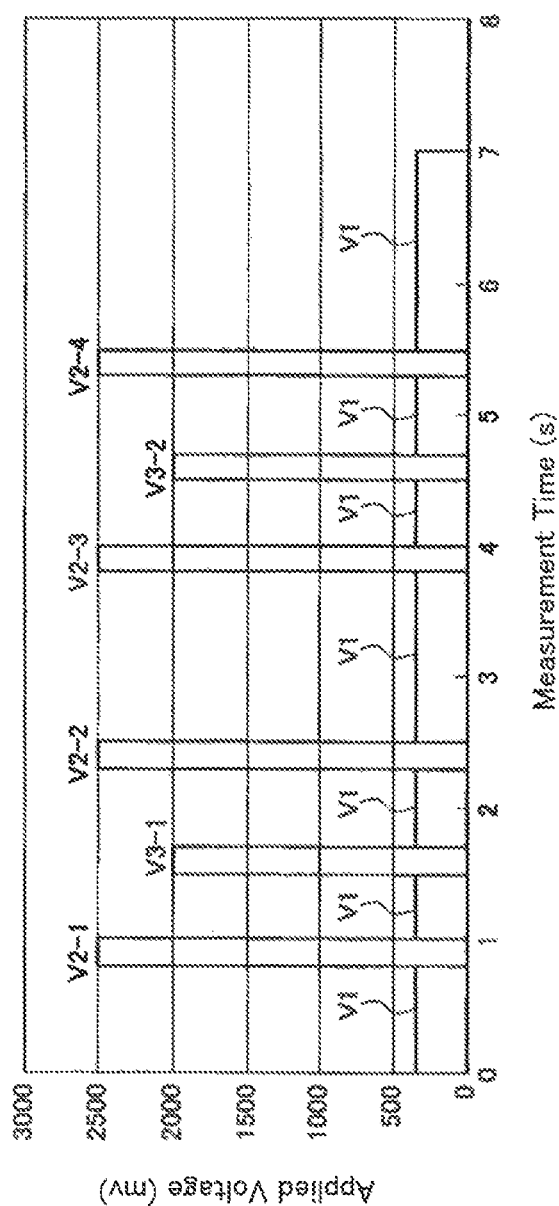
FIG. 11 is a graph showing the temporal change in voltage value in a voltage application pattern employed as a comparative example.
Figure 13:
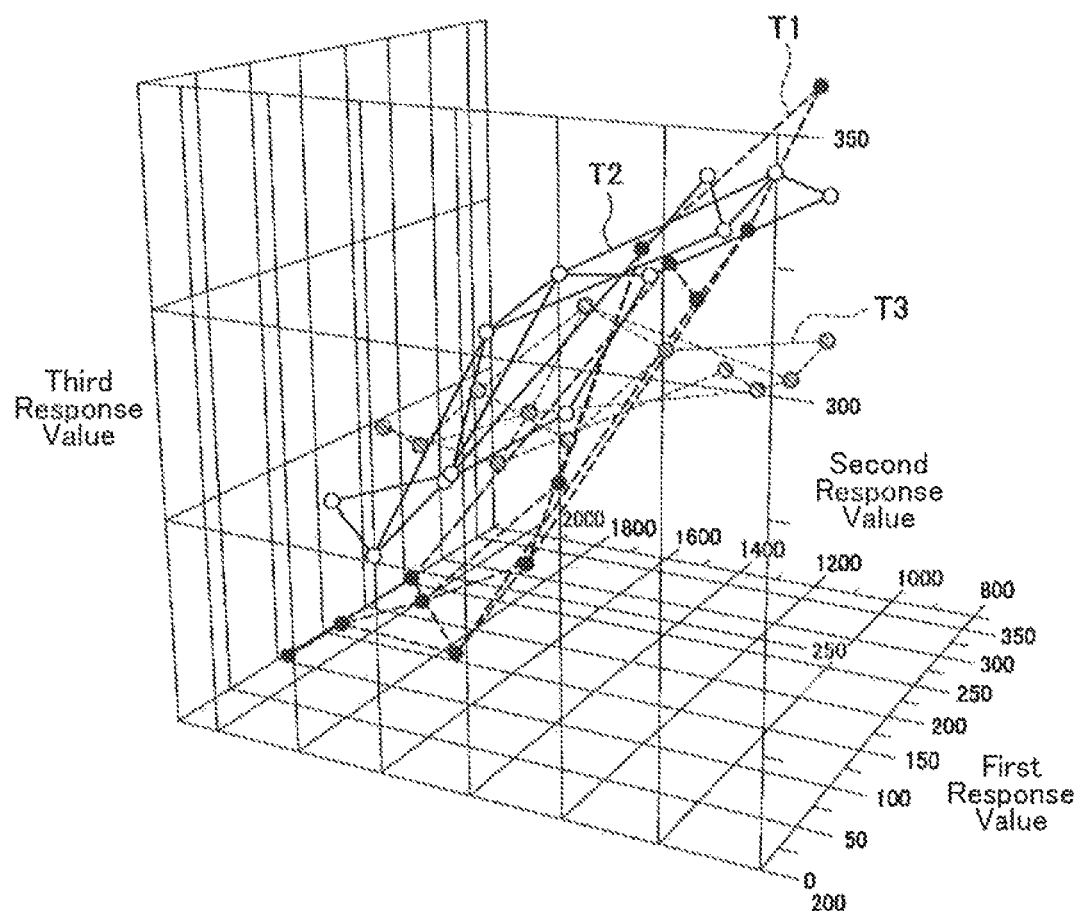
FIG. 13 is a graph showing the relationship between the first response value, the second response value, and the third response value as the comparative example.

Furthermore, it is desirable that the liquid sample measurement device 6 apply the first voltage V1 also during the application time of the third voltage V3 and the application time of the second voltage V2. For example, when the liquid sample measurement device 6 applied the first voltage V1, the second voltage V2, and the third voltage V3 at such timings and during such periods of time as shown in FIGS. 11 and 12 where the first voltage V1 was not applied during the application time of the third voltage V3 and the application time of the second voltage V2, as a result, the conversion matrices shown in FIG. 13 were obtained. According to the conversion matrices shown in FIG. 13, a plurality of conversion matrices corresponding to the respective temperatures T1, T2, and T3 of the biosensor 1 cross one another. Therefore, it is desirable that the liquid sample measurement device 6 apply the second voltage V2 and the third voltage V3 while applying the first voltage V1 to obtain the second response value and the third response value, respectively.

Figure 14:
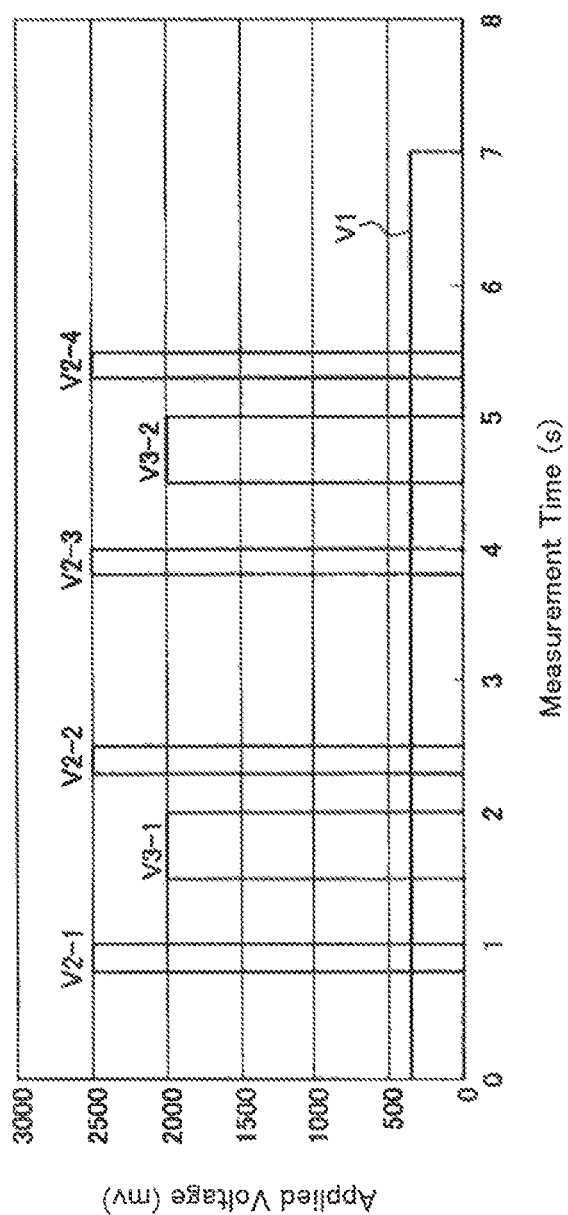
FIG. 14 is a graph showing the temporal change in voltage value in a voltage application pattern employed by a liquid sample measurement device shown as an embodiment of the present invention.
Figure 16:
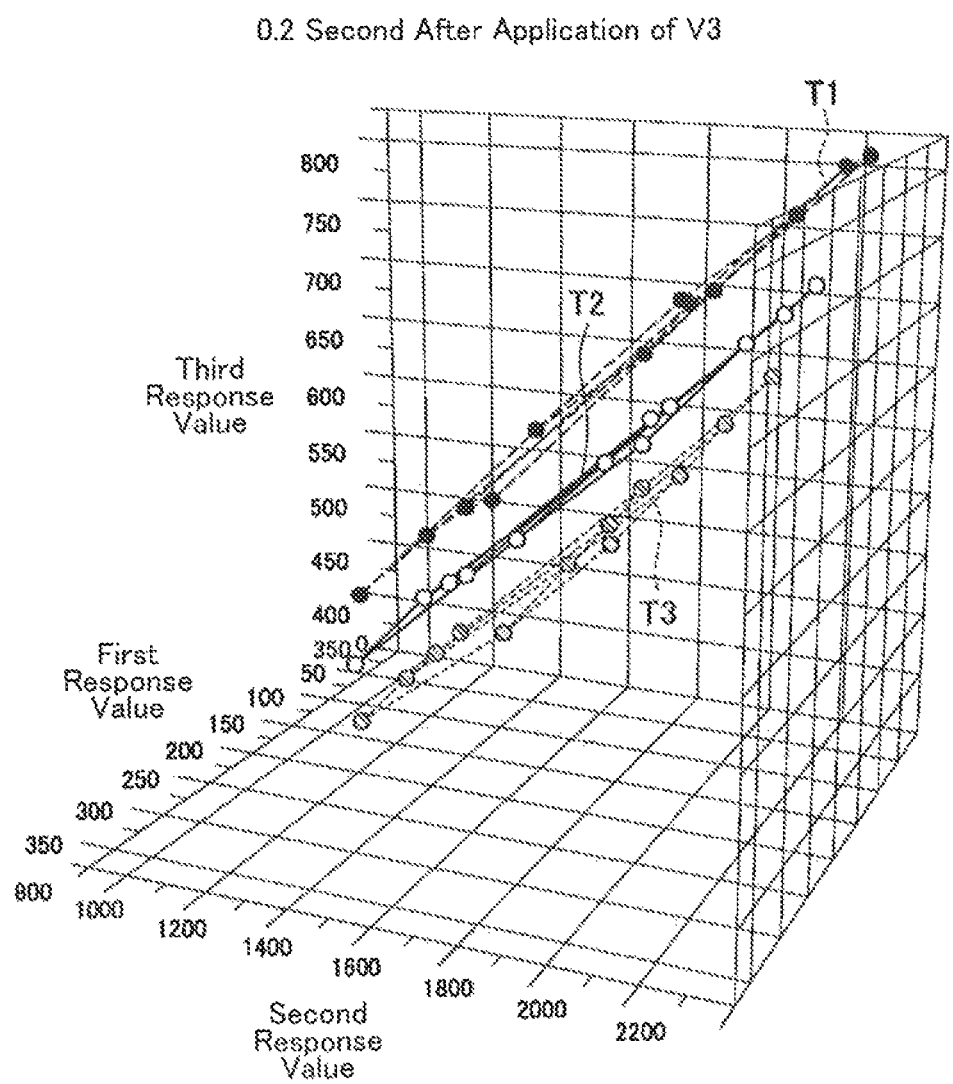
FIG. 16 is a graph showing a plurality of conversion matrices that depend on the third response value.
Figure 17:
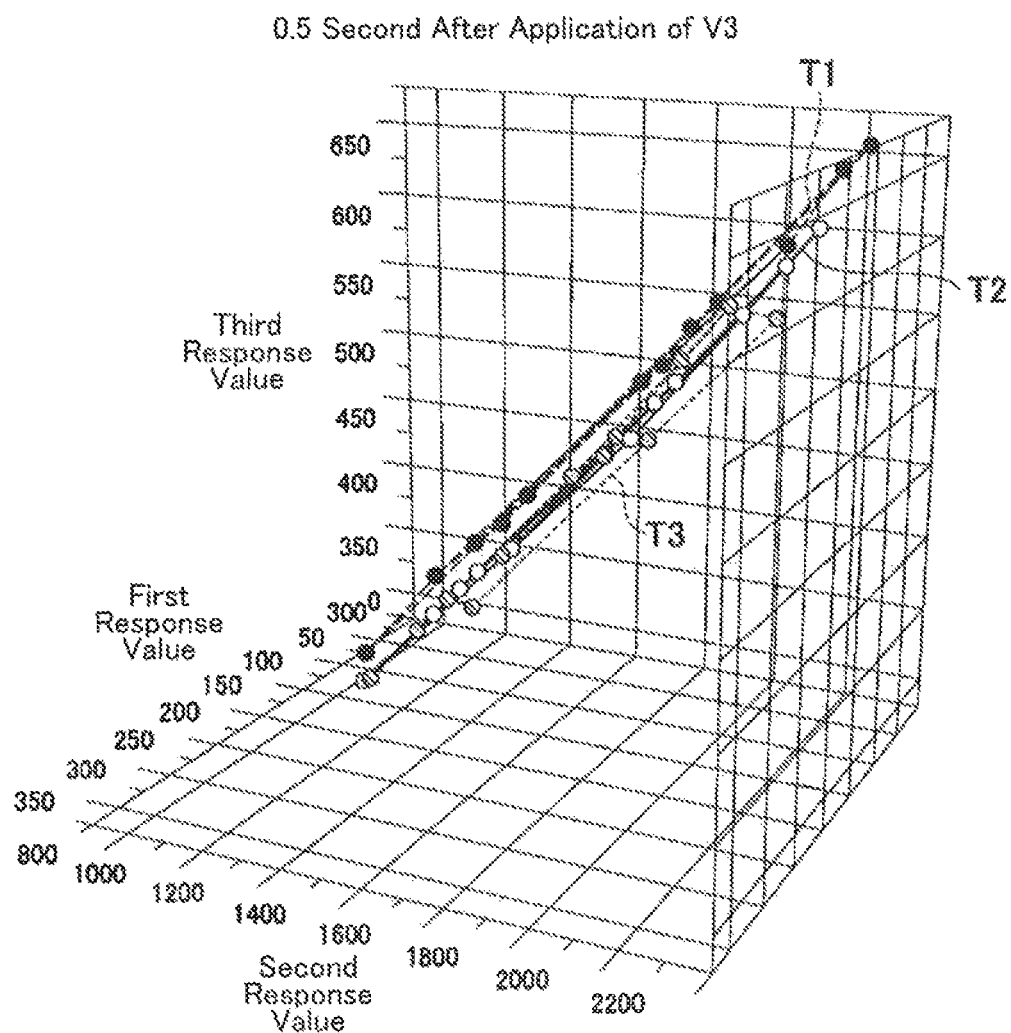
FIG. 17 is a graph showing a plurality of conversion matrices that are less dependent on the third response value.

Furthermore, the liquid sample measurement device 6 may adjust the application time of the third voltage V3 that is applied between the second working electrode 23 and the third counter electrode 27. As shown in, for example, FIG. 14, the liquid sample measurement device 6 applies the third voltage V3 far a longer period of time than that shown in FIG. 8 to obtain the third response value. The liquid sample measurement device 6 applies the first voltage V1, the second voltage V2, and the third voltage V3 at such timings and during such periods of time as shown in, for example, FIG. 15. The conversion matrices shown in FIG. 16 were obtained when the third response value was acquired 0.2 second after the third voltage V3-1 was applied. The conversion matrices shown in FIG. 17 were obtained when the third response value was acquired 0.5 second after the third voltage V3-1 was applied. Thus, when acquiring the third response value immediately after the third voltage V3-1 was applied, the liquid sample measurement device 6 can obtain transfer matrices in which the third response value varies significantly per temperature of the biosensor 1. That is, as shown in FIG. 16, the liquid sample measurement device 6 can obtain conversion matrices of the temperatures T1, T2, T3 of the biosensor 1 that do not cross one another.

Figure 18:
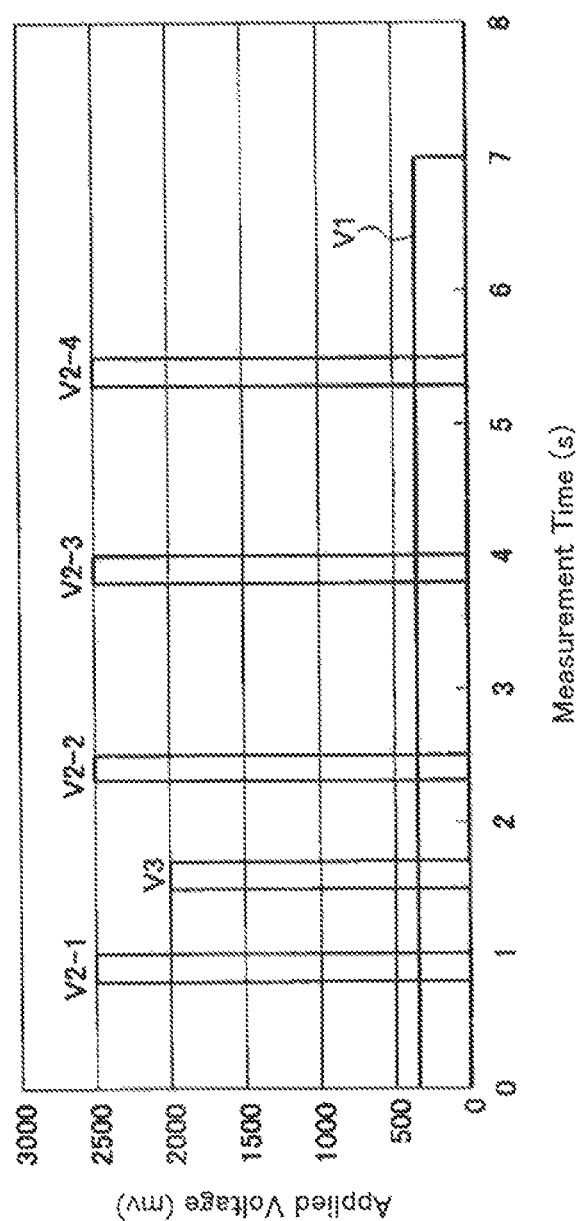
FIG. 18 is a graph showing the temporal change in voltage value in a voltage application pattern employed by a liquid sample measurement device shown as an embodiment of the present invention.
Figure 19:
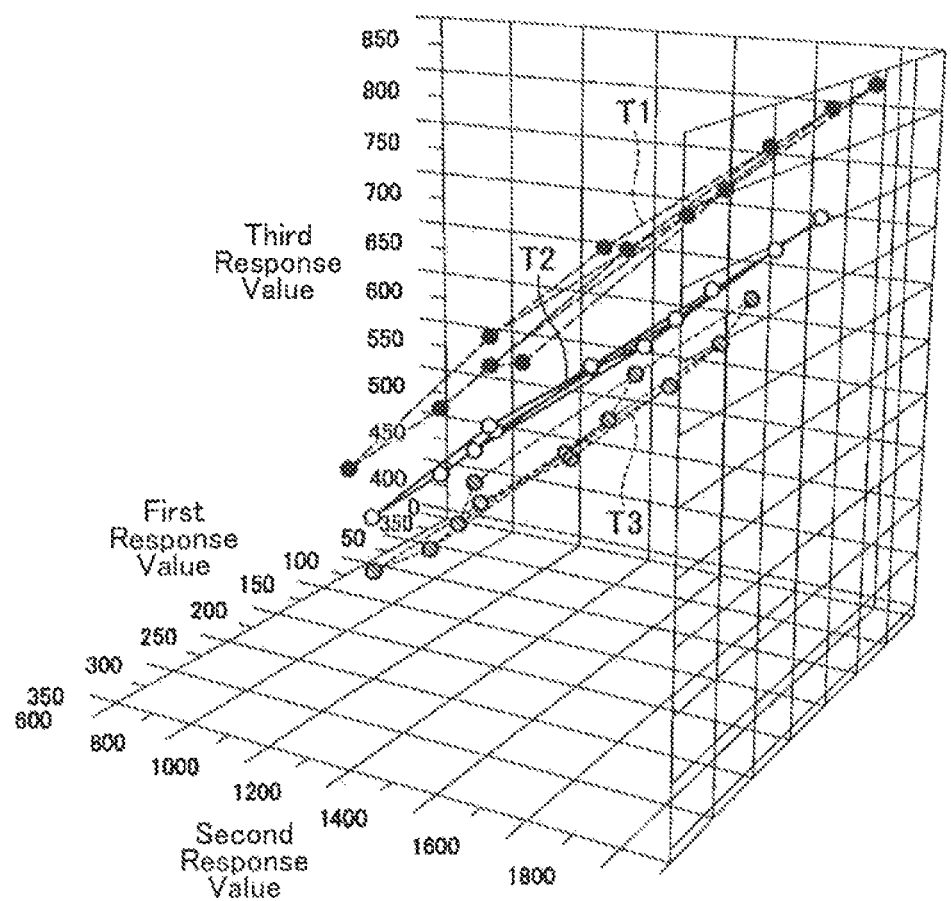
FIG. 19 is a graph showing a plurality of conversion matrices that are obtained when voltages are applied as shown in FIG. 18 in the liquid sample measurement device shown as an embodiment of the present invention.

Furthermore, it is desirable that the liquid sample measurement device 6 apply the third voltage V3 after the second voltage V2 is applied. For example, as shown in FIG. 18, the liquid sample measurement device 6 applies the third voltage V3 after the first second voltage V1-1 is applied. Then, as shown in FIG. 19, the liquid sample measurement device 6 can obtain conversion matrices of the temperatures T1, T2, T3 of the biosensor 1 that do not cross one another.

Figure 20:
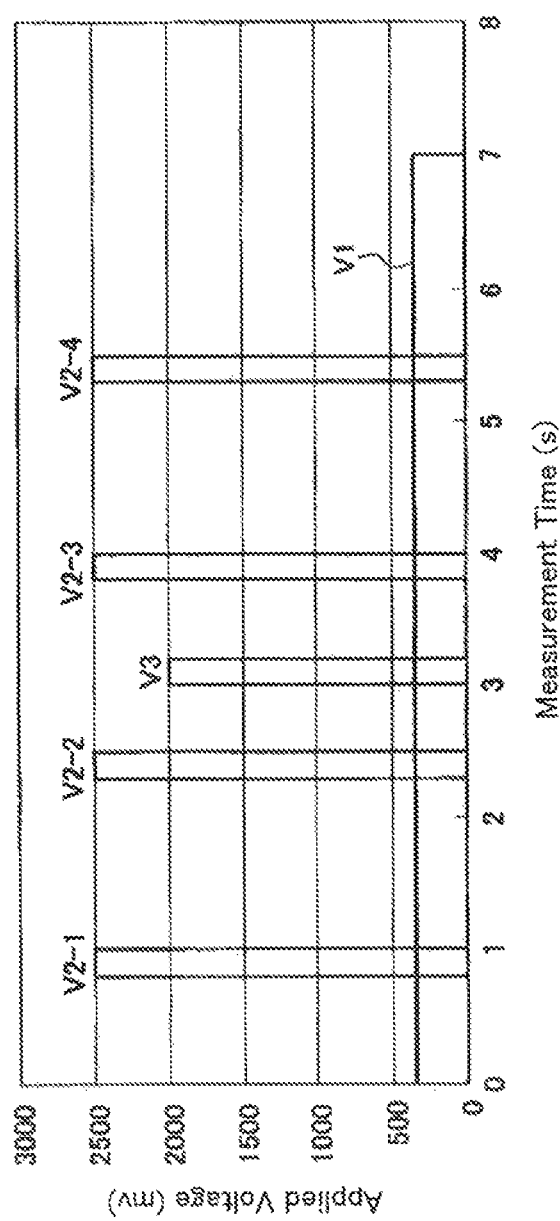
FIG. 20 is a graph showing the temporal change in voltage value in a voltage application pattern employed by a liquid sample measurement device shown as an embodiment of the present invention.
Figure 21:
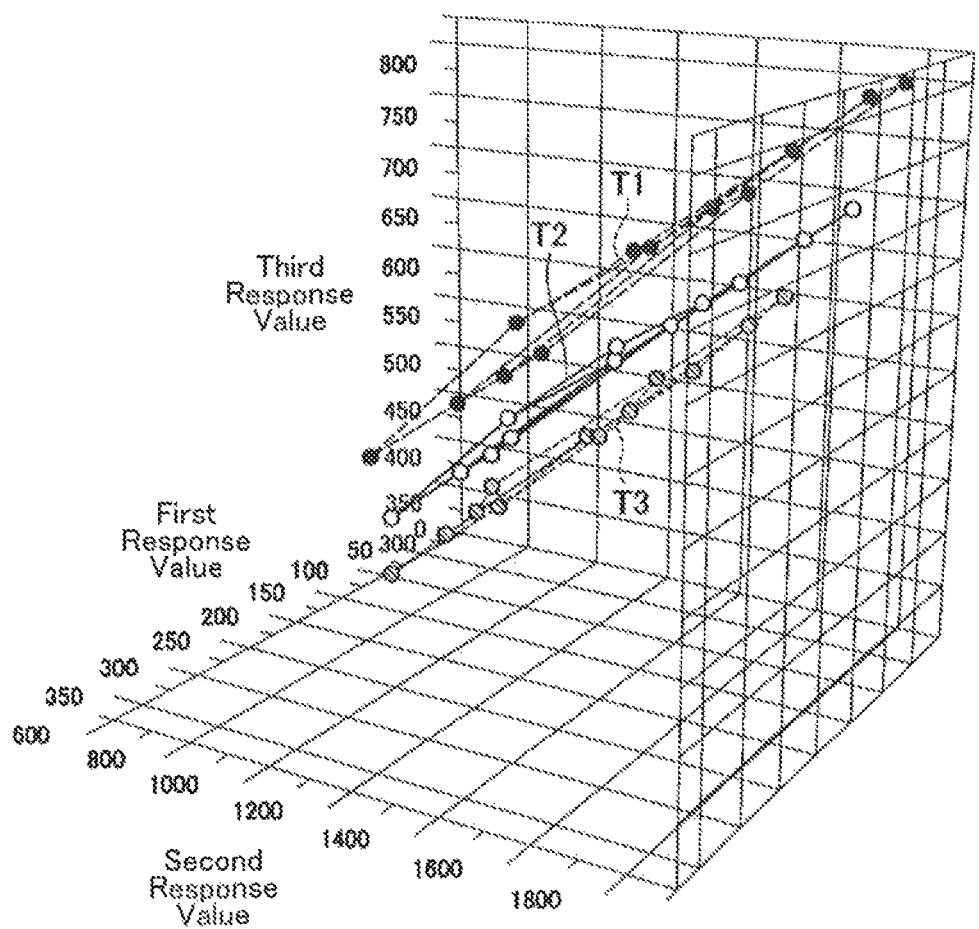
FIG. 21 is a graph showing a plurality of conversion matrices that are obtained when voltages are applied as shown in FIG. 20 in the liquid sample measurement device shown as an embodiment of the present invention.
Figure 22:
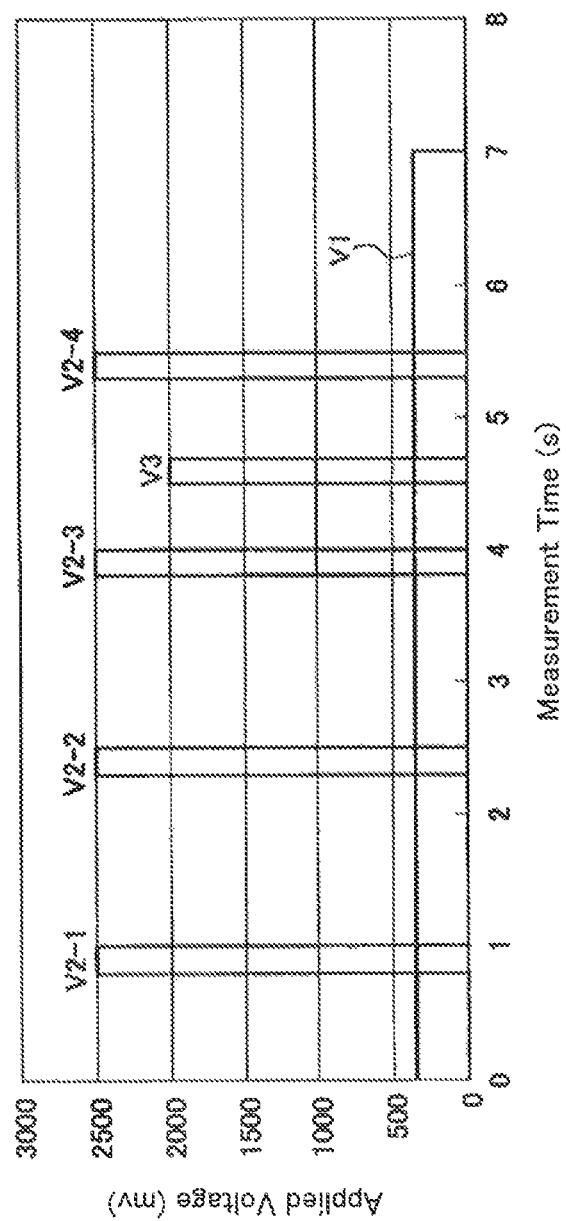
FIG. 22 is a graph showing the temporal change in voltage value in a voltage application pattern employed by a liquid sample measurement device shown as an embodiment of the present invention.
Figure 23:
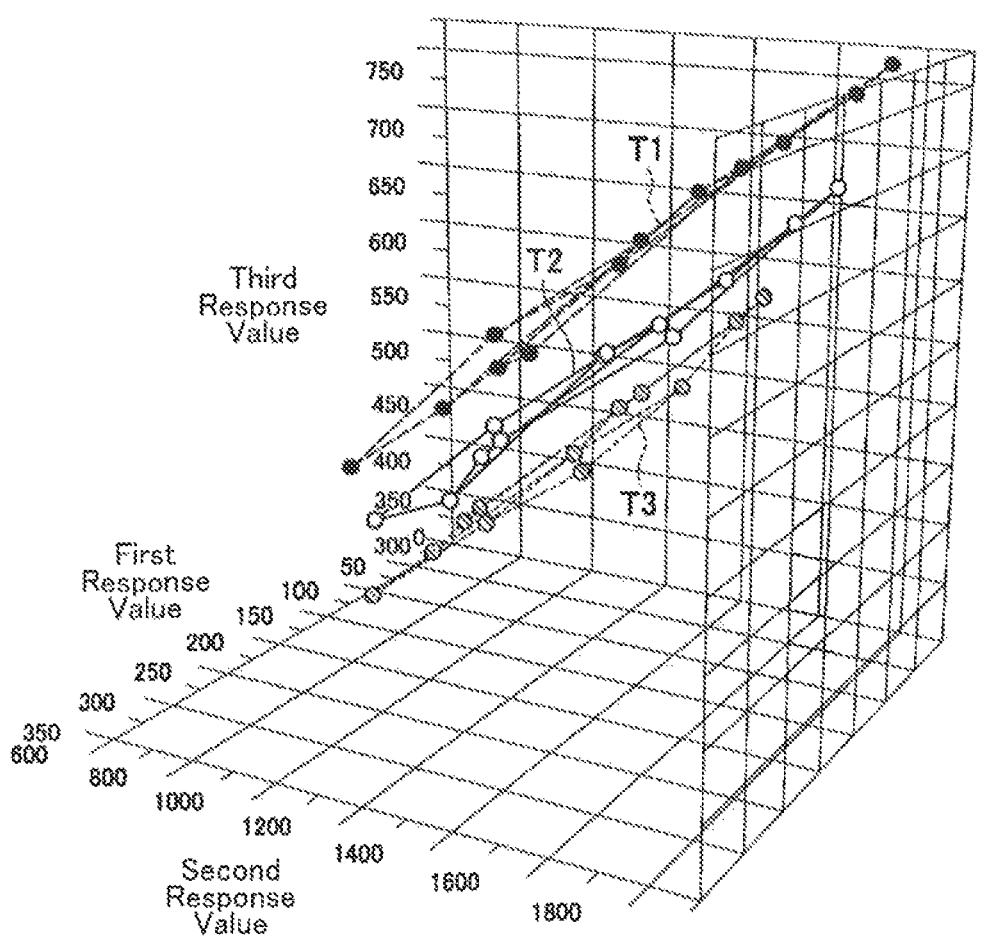
FIG. 23 is a graph showing a plurality of conversion matrices that are obtained when voltages are applied as shown in FIG. 22 in the liquid sample measurement device shown as an embodiment of the present invention.

As shown in FIG. 20, it is desirable that the liquid sample measurement device 6 apply the third voltage V3 after the second voltage V2-2 is applied. Also in this case, as shown in FIG. 21, the liquid sample measurement device 6 can obtain the concentration of glucose and the amount of blood cells of the unknown blood as well as the value equivalent to the temperature of the biosensor 1, using the conversion matrices of the temperatures T1, T2, T3 of the biosensor 1 that do not cross one another. For example, as shown in FIG. 22, the liquid sample measurement device 6 applies the third voltage V3 after the third second voltage V2-3 is applied. Also in this case, as shown in FIG. 23, the liquid sample measurement device 6 can obtain conversion matrices of the temperatures T1, T2, T3 of the biosensor 1 that do not cross one another.

Figure 24:
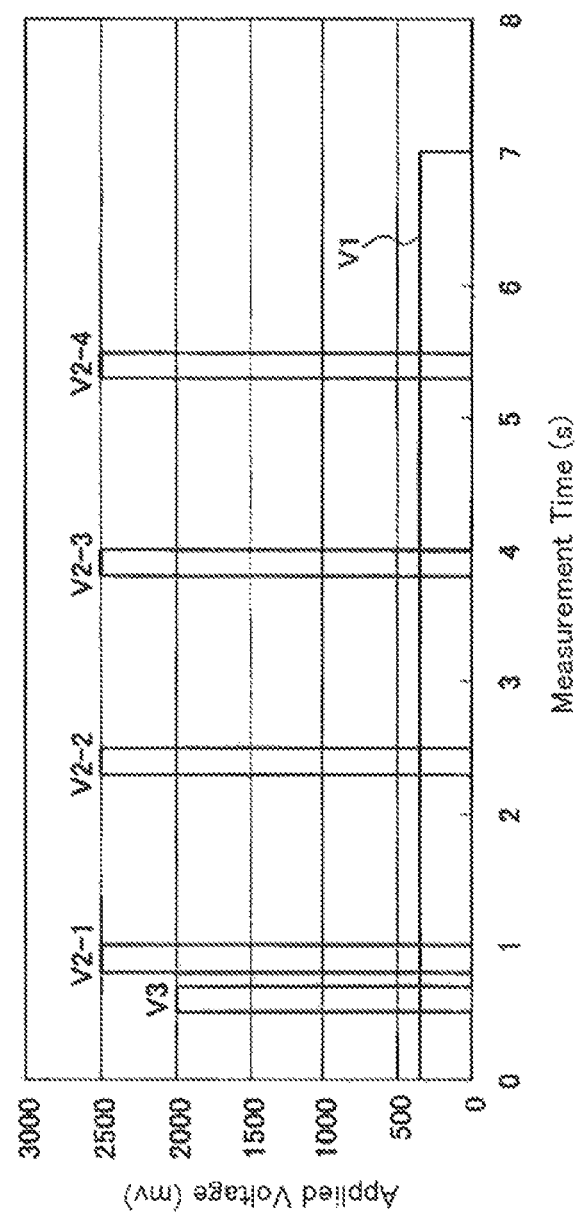
FIG. 24 is a graph showing the temporal change in voltage value in a voltage application pattern used as a comparative example.
Figure 25:
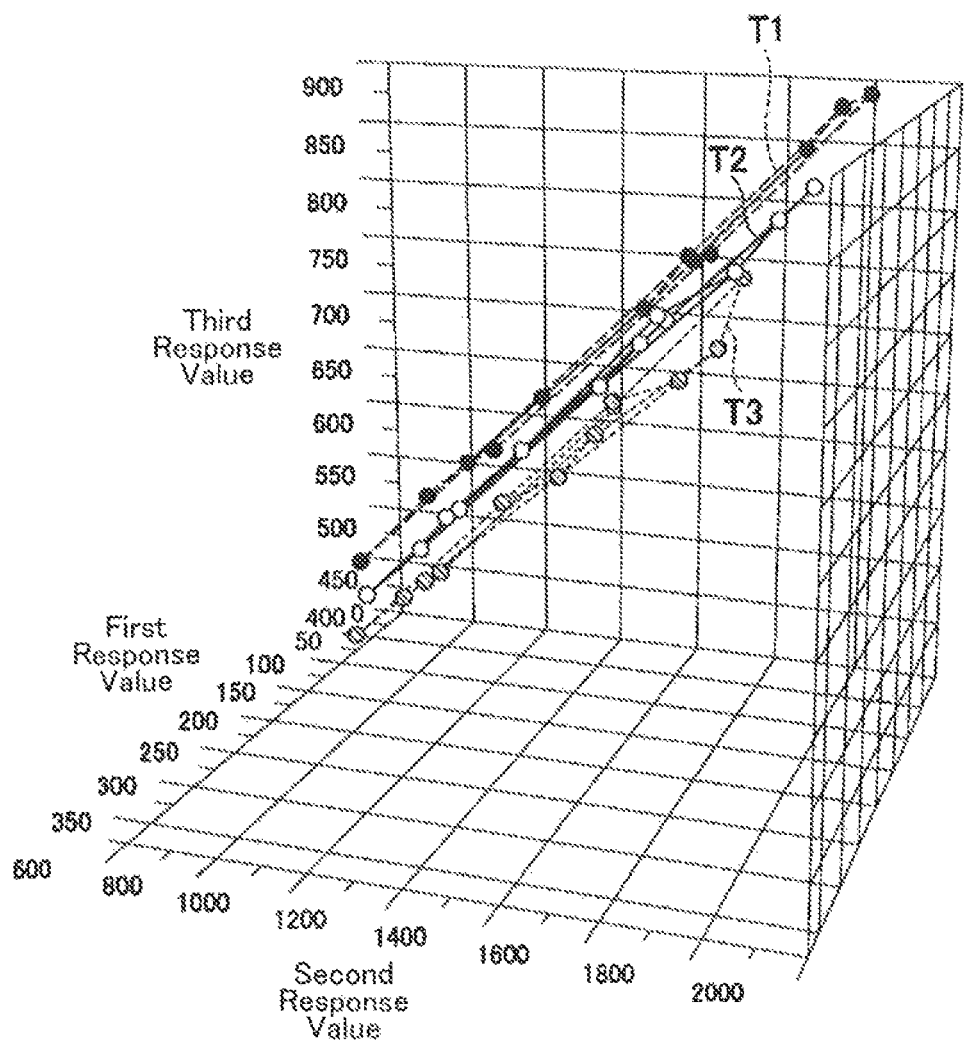
FIG. 25 is a graph showing a plurality of conversion matrices that are obtained when voltages are applied as shown in FIG. 24.

On the other hand, as shown in FIG. 24, when applying the third voltage V3 before the first second voltage V2-1 was applied, the liquid sample measurement device 6 obtained conversion matrices per temperature T1, T2, T3 of the biosensor 1 in which the difference in third response value was small as shown in FIG. 25. Accordingly, it is desirable that the liquid sample measurement device 6 apply the third voltage V3 after the second voltage V2.

Figure 26:
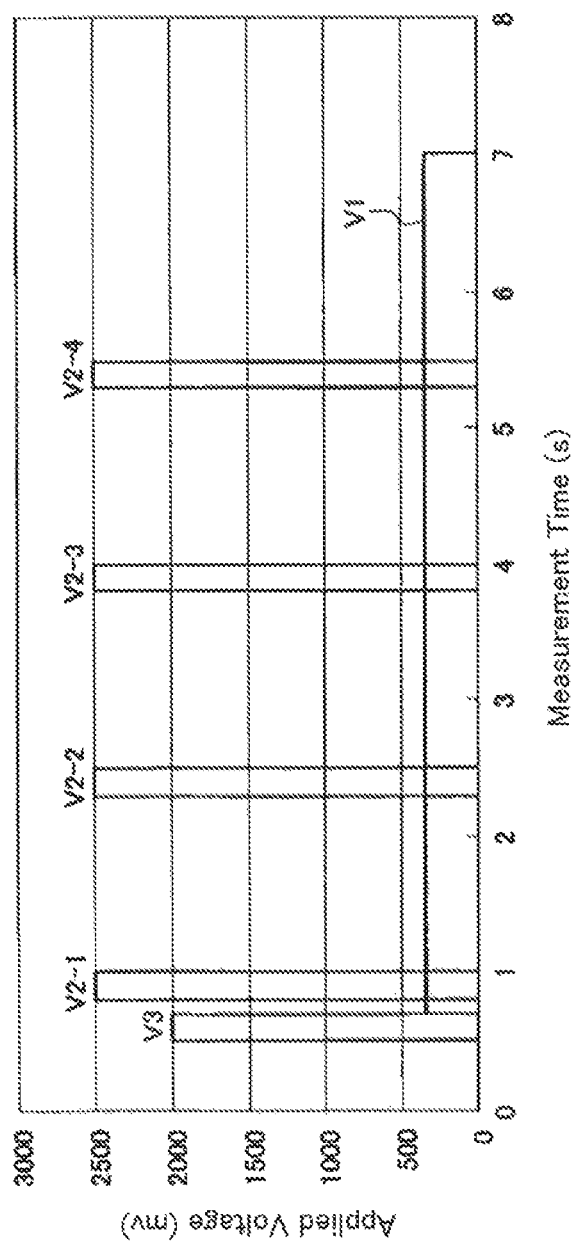
FIG. 26 is a graph showing the temporal change in voltage value in a voltage application pattern used as a comparative example.
Figure 27:
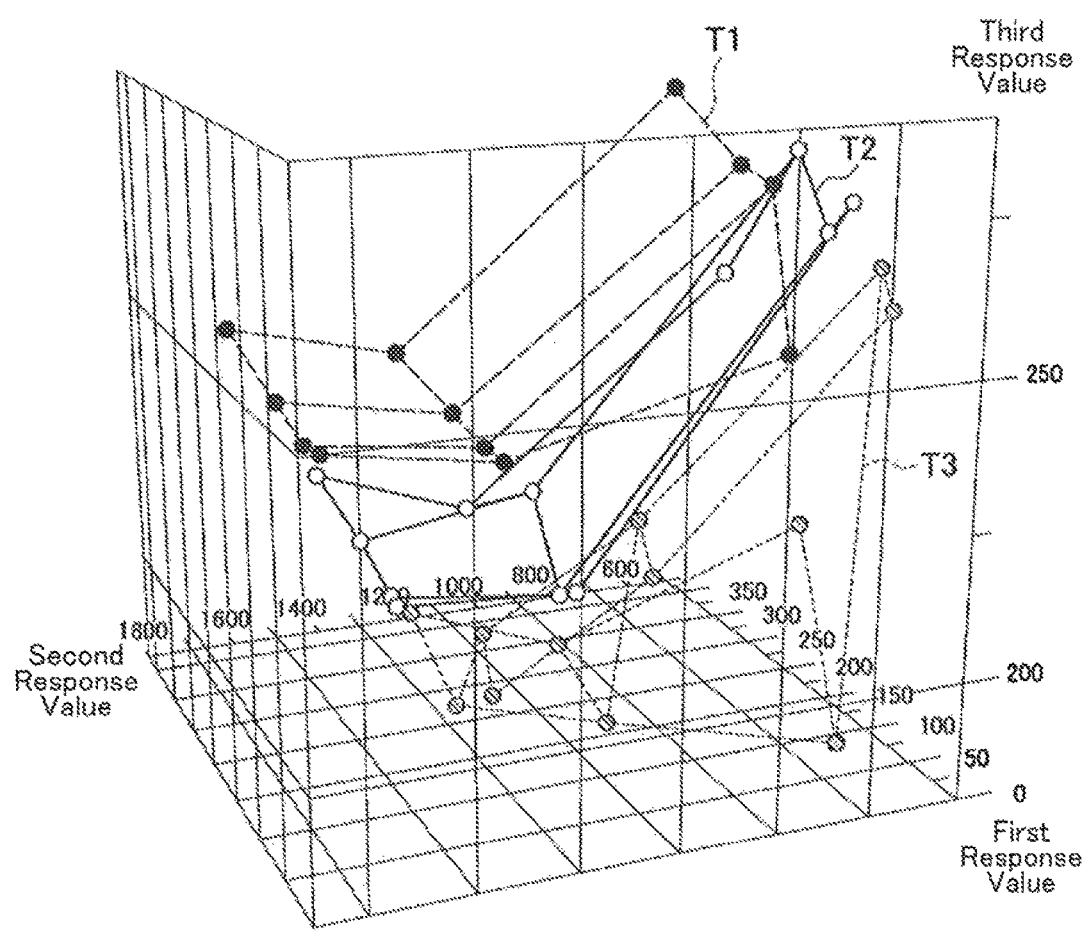
FIG. 27 is a graph showing a plurality of conversion matrices that are obtained when voltages are applied as shown in FIG. 26.

Furthermore, as shown in FIG. 26, when the liquid sample measurement device 6 applies the third voltage V3 before applying the first second voltage V2-1 while not applying the first voltage V1, the conversion matrices obtained per temperature T1, T2, T3 of the biosensor 1 cross one another as shown in FIG. 27. Therefore, it is desirable that the liquid sample measurement device 6 apply the third voltage V3 while applying the first voltage V1.

Figure 28:
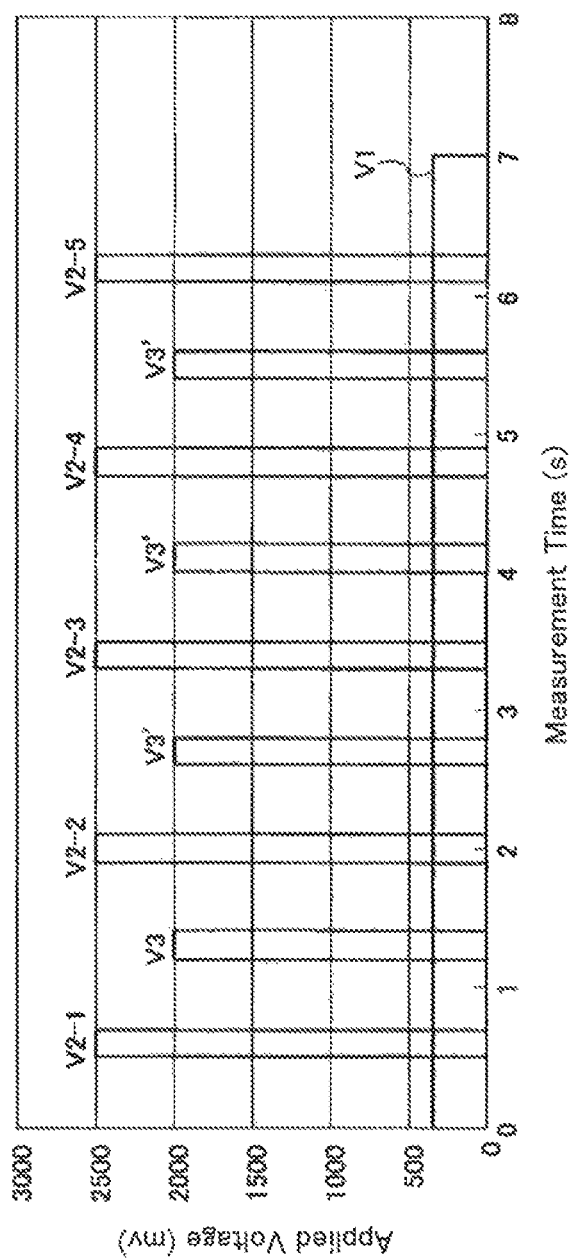
FIG. 28 is a graph showing the temporal change in voltage value in a voltage application pattern employed by a liquid sample measurement device shown as an embodiment of the present invention.
Figure 30:
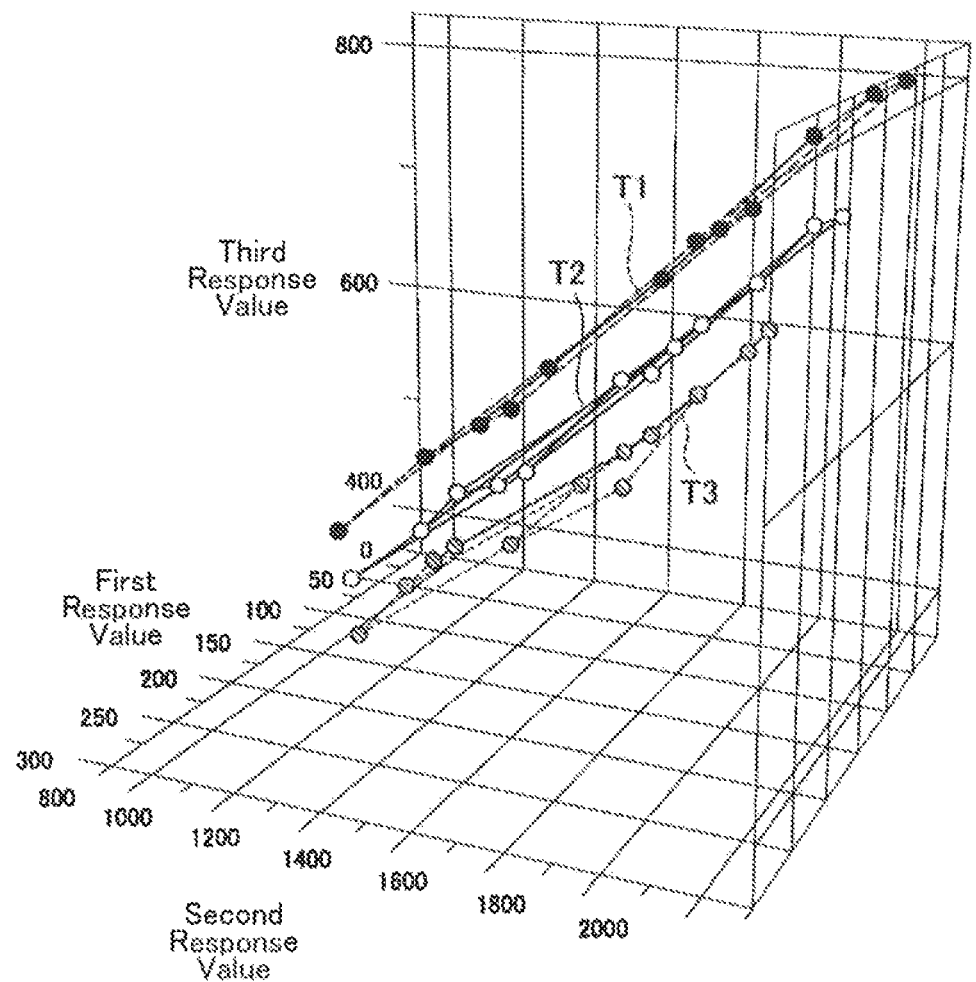
FIG. 30 is a graph showing a plurality of conversion matrices that are obtained when voltages are applied as shown in FIGS. 28 and 29 in the liquid sample measurement device shown as an embodiment of the present invention.

Furthermore, when applying the third voltage V3, the liquid sample measurement device 6 used the second working electrode 23 as the working electrode while using the third counter electrode 27 as the counter electrode, but they may be used inversely. For example, the liquid sample measurement device 6 applies the third voltage V3 as shown in FIG. 28. In this case, as shown in FIGS. 28 and 29, the liquid sample measurement device 6 applies the first third voltage V3, with the second working electrode 23(A) being used as the working electrode and the third counter electrode 27(F) being used as the counter electrode. On the other hand, the liquid sample measurement device 6 applies the second to fourth third voltages V3', with the second working electrode 23(A) being used as the counter electrode and the third counter electrode 27(F) being used as the working electrode. As described above, even when applying the third voltages V3 and V3' to obtain the third response values, the liquid sample, measurement device 6 can obtain conversion matrices of the temperatures T1, T2, T3 of the biosensor 1 that do not cross one another as shown in FIG. 30.

Figure 31:
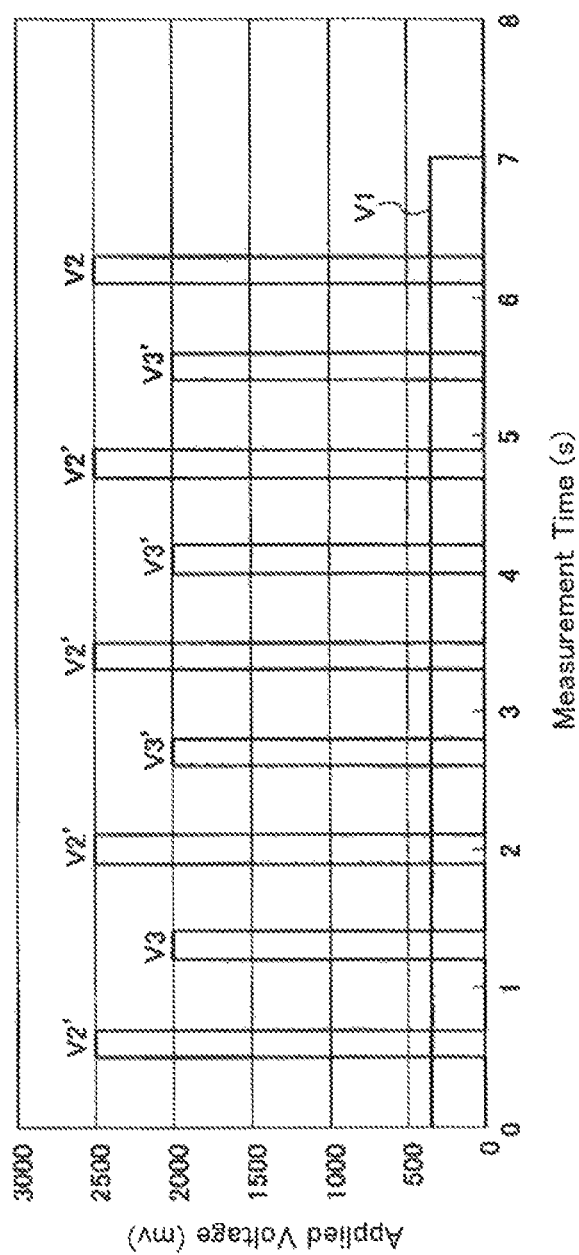
FIG. 31 is a graph showing the temporal change in voltage value in a voltage application pattern employed by a liquid sample measurement device shown as an embodiment of the present invention.
Figure 33:
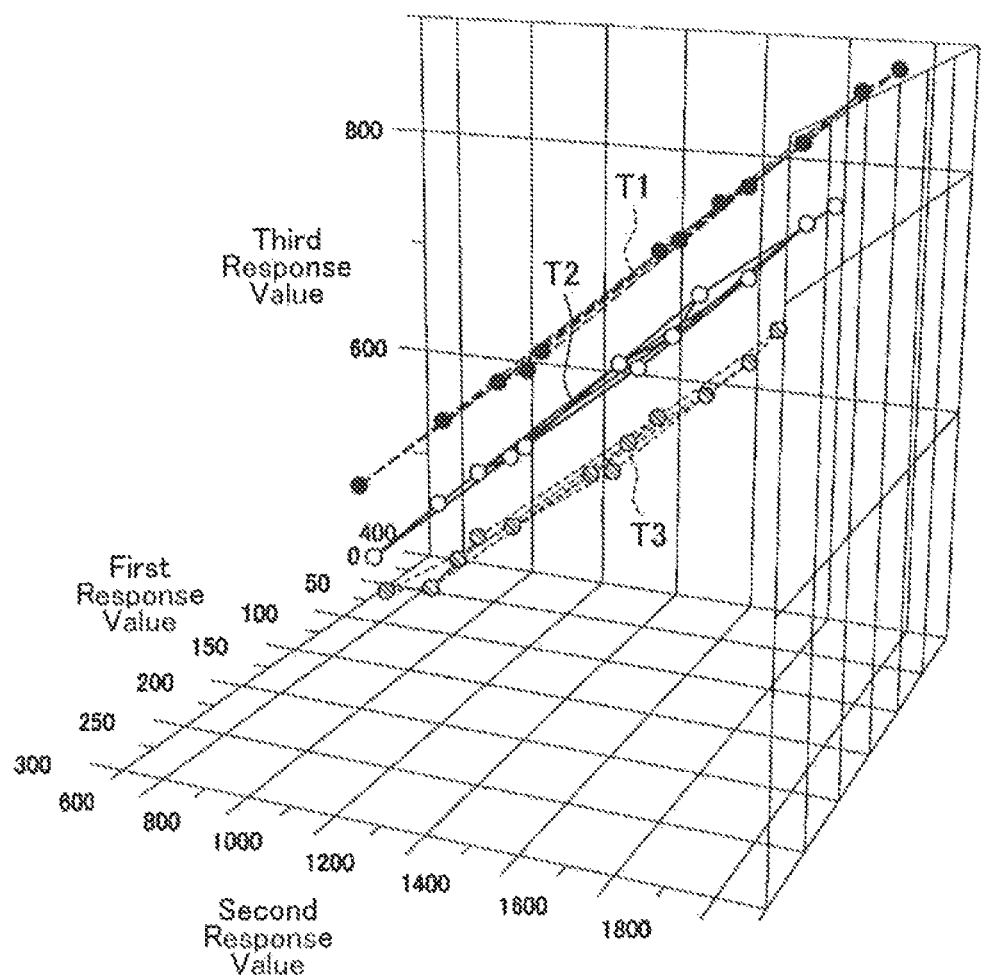
FIG. 33 is a graph showing a plurality of conversion matrices that are obtained when voltages are applied as shown in FIGS. 31 and 32 in the liquid sample measurement device shown as an embodiment of the present invention.

Furthermore, the liquid sample measurement device 6 is not limited to the embodiment described above, and the electrodes to which the second voltage V2 is applied may be changed. In the embodiment described above, the second voltage V2 was applied, between the second working electrode 23(A) and the second counter electrode 24(G). Furthermore, the third voltage V3 was applied between the second working electrode 23(A) and the third counter electrode 27(F). However for example, the liquid sample measurement device 6 that applies the second voltage V2 and the third voltage V3 as shown in FIG. 31 applies the second voltage to another electrode pair. For example, as shown in FIG. 32, the liquid sample measurement device 6 applies a second voltage V2', with the third counter electrode 27(F) being used as the working electrode and the second counter electrode 24(G) being used as the counter electrode. In this manner, even when applying the second voltage V2 to obtain the second response values, the liquid sample measurement device 6 can obtain conversion matrices of the temperatures T1, T2, T3 of the biosensor 1 that do not cross one another as shown in FIG. 33.

Figure 34:
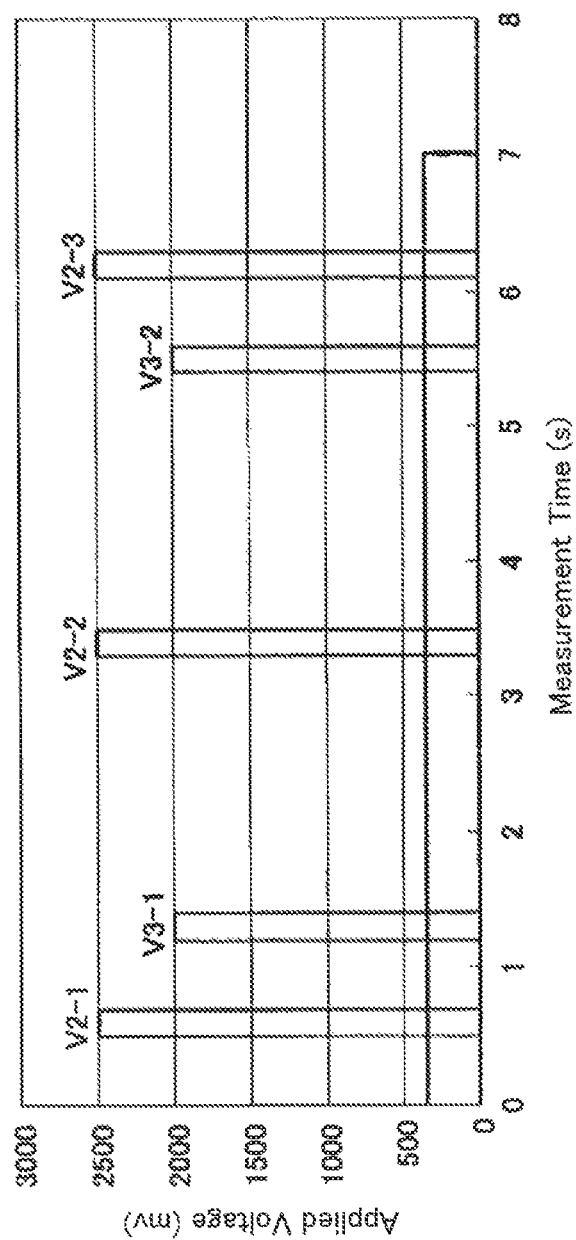
FIG. 34 is a graph showing the temporal change in voltage value in a voltage application pattern used as a comparative example.
Figure 36:
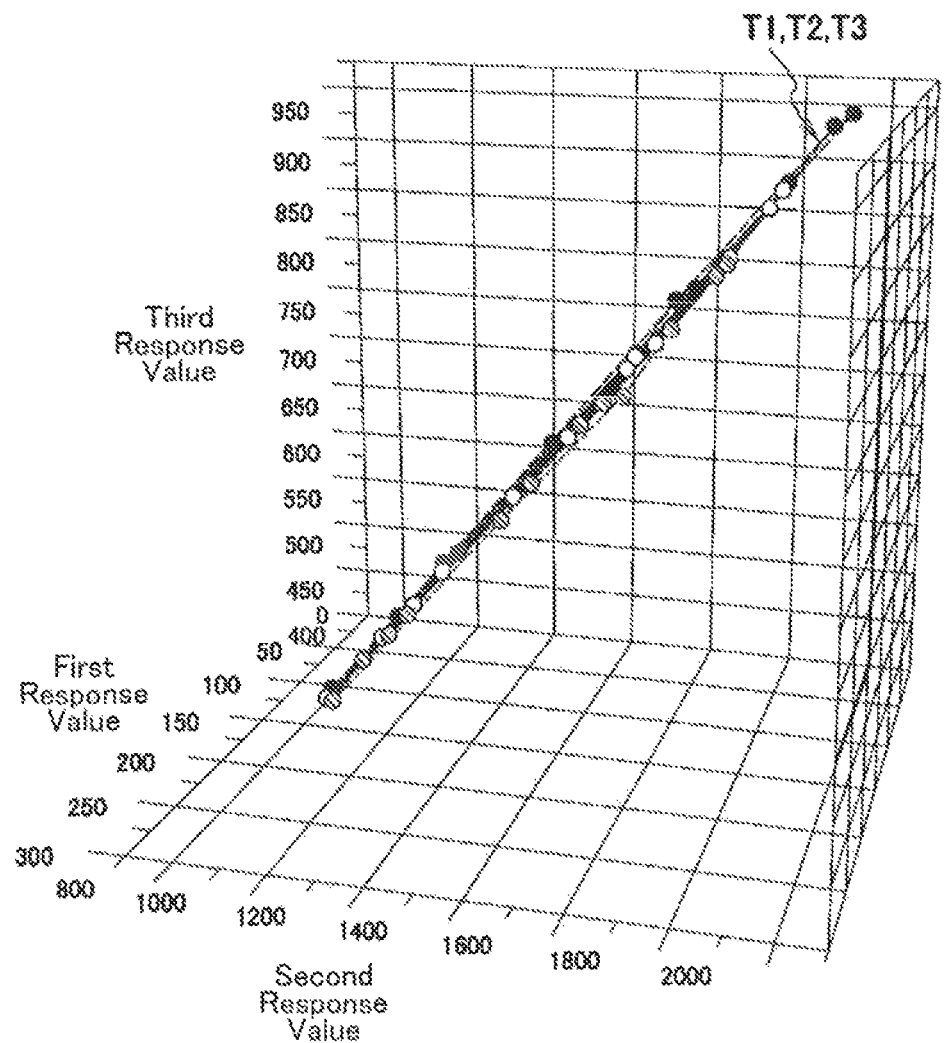
FIG. 36 is a graph showing a plurality of conversion matrices that are obtained when voltages are applied as shown in FIGS. 34 and 35.

Furthermore, it is desirable that in the liquid sample measurement device 6, the electrode pair to which the third voltage V3 is applied be different from the electrode pair to which the second voltage V2 is applied. For example, as shown in FIG. 34, the liquid sample measurement device 6 applies the second voltage V2-1, the third voltage V3-1, the second voltage V2-2, the third voltage V3-2, and the second voltage V2-3 in this order after starting the measurement. In this case, for example, as shown in FIG. 35, the liquid sample measurement device 6 applies the second third voltage V3-2 to the third counter electrode 27(F) and the second working electrode 23(A). For example, the liquid sample measurement device 6 applies the second voltage V2 and the third voltage V3-1 other than the second third voltage V3-2 between the second working electrode 23(A) and the second counter electrode 24(G). That is, the second voltage V2 is applied to the second working electrode 23(A) and the second counter electrode 24(G). Furthermore, as the third voltage V3-1, a voltage with the same value as that of the third voltage V3-2 is applied between the second working electrode 23(A) and the second counter electrode 24(G). Then, the third response value does not vary much even at different temperatures of the biosensor 1. Accordingly, as shown in FIG. 36, the conversion matrices of the temperatures T1, T2, T3 of the biosensor 1 overlap with one another in the same place. Therefore, it is desirable that the liquid sample measurement device 6 apply the second voltage V2 and the third voltage V3 to different electrode pairs, respectively.

As described in detail above, according to the liquid sample measurement device 6 shown as the present embodiment the concentration of glucose and the amount of blood cells of blood as well as the value equivalent to the temperature of the biosensor 1 can be measured using the first response value, the second response value, and the third response value.

Figure 37:
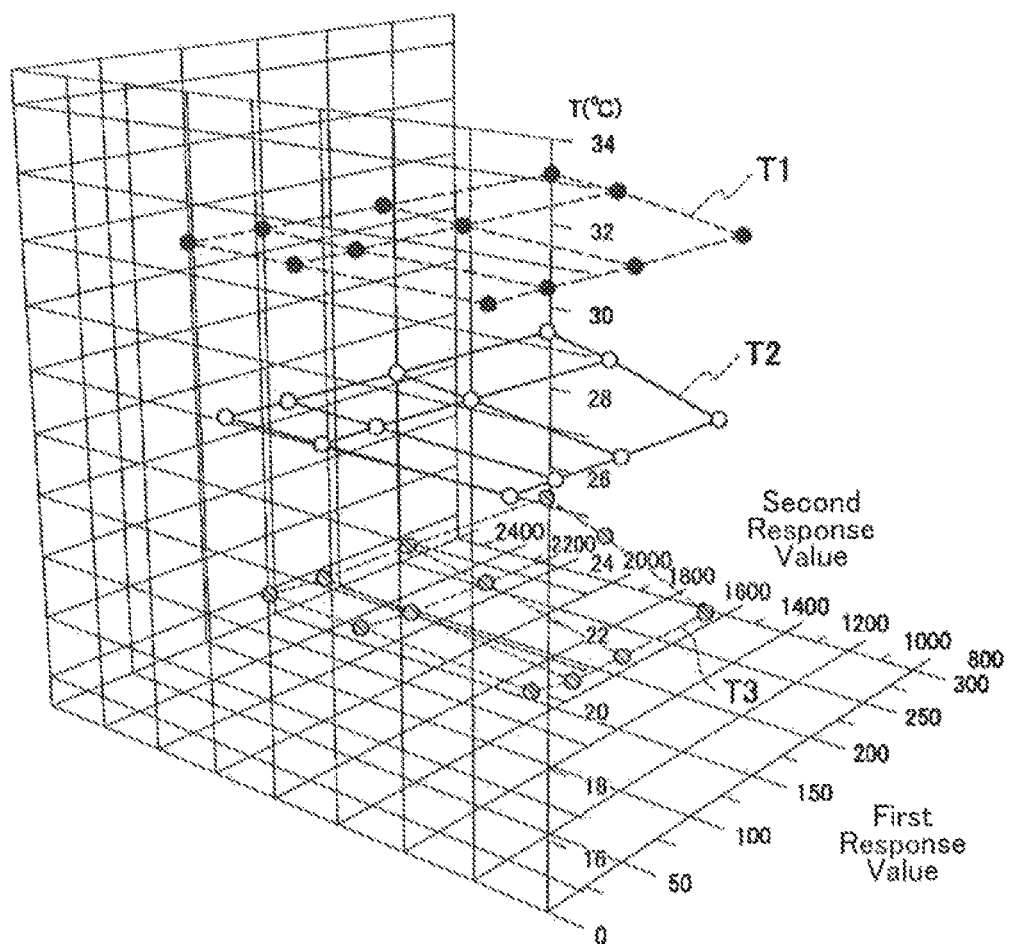
FIG. 37 is a graph showing conversion matrices as a comparative example.

On the other hand, for example, when the conversion matrices of the first response value and the second response value were prepared per temperature, the temperature (° C.) of the biosensor 1 must be constant in each conversion matrix as shown in FIG. 37. In this case, when the temperature obtained by the liquid sample measurement device 6 deviates from the temperature of the portion where the first and second response values are actually measured, it is difficult to obtain accurate conversion values since there is no means for reflecting that information. On the other hand, the liquid sample measurement device 6 of the present invention can refer to conversion matrices obtained using not only the first response value and the second response value but also the third response value added thereto to determine the glucose conversion value, the blood cell amount conversion value, and the value equivalent to the temperature of the biosensor 1. Therefore, with the liquid sample measurement device 6 of the present invention, the glucose conversion value can be obtained with a high accuracy.

Furthermore, the liquid sample measurement device 6 is provided with, for example, a third counter electrode 27 to obtain the third response value and applies the third voltage between said third counter electrode 27 (the counter electrode) and the second working electrode 23 (the working electrode). Thus, the liquid sample measurement device 6 can detect, as the third response value, the current obtained by applying the third voltage between the second working electrode 23 and the third counter electrode 27. Also this allows the liquid sample measurement device 6 to obtain the third response value that is considered to depend on the temperature of the reaction part of the biosensor 1. Therefore, the liquid sample measurement device 6 can calculate the concentration of glucose using not only the first response value that mainly depends on the concentration of glucose and the second response value that mainly depends on the amount of blood cells but also the third response value that depends on the temperature of the biosensor 1 to a high degree.

Moreover, it is desirable that the liquid sample measurement device 6 obtain the third current value (the third response value) while applying the first voltage. In this case, as described with reference to FIG. 11 or FIG. 13, conversion matrices that do not overlap with one another in the direction of the third response value are obtained, and using these conversion matrices, the concentration of glucose and the amount of blood cells of blood as well as the value equivalent to the temperature of the biosensor 1 can be obtained.

Furthermore, it is desirable that the liquid sample measurement device 6 obtain the third current value (the third response value) after applying the second voltage. In this case, as described with reference to FIG. 18 or FIG. 27, conversion matrices that do not overlap with one another are obtained, and using these conversion matrices, the concentration of glucose and the amount of blood cells of blood as well as the value equivalent to the temperature of the biosensor 1 can be obtained.

Moreover the liquid sample measurement device 6 stores recorded data in which, for example, per temperature and liquid containing the first component and the second component whose amounts are known, the first current value, the second current value, and the third current value obtained with respect to the liquid are recorded. Then, the liquid sample measurement device 6 compares the above-mentioned recorded data with measured data containing the first current value, the second current value, and the third current value and thereby can calculate, as the amount of the first component of the liquid introduced into the biosensor 1, the amount of the first component of the liquid from which the recorded data most approximated to said measured data was obtained. Similarly, by comparing the recorded data with the measured data, the liquid sample measurement device 6 can calculate, as the amount of blood cells of the blood subjected to the measurement and the value equivalent, to the temperature of the biosensor 1, the amount of blood cells and the value equivalent to the temperature of the biosensor 1 that are most approximated to the measured data. Thus, the liquid sample measurement device 6 can obtain, a highly accurate concentration of glucose and amount of blood cells of the blood as well as the value equivalent to the temperature of the biosensor 1 merely through the calculation for comparing the first response value, the second response value, and the third response value of the recorded data with those of the measured data, respectively.

Furthermore, according to a liquid sample measurement device 6 in which, for example, the electrode pair (the third electrode pair) for obtaining the third response value is composed of a first electrode that does not contact blood and an electrode that does not contact a liquid and that is selected from the electrode pair for measuring the second response value, a third response value that depends mainly on the temperature of the reaction part of the biosensor 1 can be obtained.

The above-mentioned embodiments are examples of the present invention. Therefore, the present invention is not limited to the above-mentioned embodiments, and it should be appreciated that various changes can be made thereto according to the designs, etc. as long as the changes remain within the scope of the present invention without departing from the technical concept thereof even in embodiments other than the present embodiments.

In the above-mentioned liquid sample measurement device 6, the third voltage was applied to the third electrode pair in order to obtain the third current value (the third response value) but another method may be used to obtain the third current value. The CPU 74 may control the first voltage value to be applied between the first working electrode 21 and the first counter electrode 22 for measuring the first current value to obtain a third current value that is different from the first current value and the second current value. The CPU 74 refers to the values determined by, for example, tests beforehand to apply the first voltage between the first working electrode 21 and the first counter electrode 22 and thereby can obtain the third current value. As described above, the first voltage set so as to be considered to mainly depend on the temperature of the biosensor 1 is applied and thereby the third circuit value is obtained. With respect to the first voltage to be applied to obtain the third response value, a voltage value within a predetermined range, a predetermined application timing, and a predetermined application time that have been determined by, for example, tests beforehand are selected.

For example, the first voltage to be applied to obtain the first response value is about 1 to 600 mV. Such a range of the first voltage is a voltage range suitable for oxidation-reduction of blood. On the other hand, the first voltage to be applied to obtain a third response value that tends to depend on the temperature of the biosensor 1 is higher than the voltage to be applied to obtain a first response value of 600 mV and it is preferably 2000 mV. With application, of the first voltage to be applied to obtain the third response value, a current value that highly depends on the temperature of the biosensor 1 can be obtained by tests in which a liquid is introduced into the biosensor 1. The first voltage to be applied to obtain the high third response value is in the range of voltages that allow water to be electrolyzed. Therefore, when applying the first voltage to obtain the temperature equivalent value, for example, the liquid sample measurement device 6 measures the first response value and thereafter applies the first voltage that is higher than the first response value to obtain the third response value.

As described above, the liquid sample measurement device 6 shown as the present embodiment can control the first voltage V1 to obtain the third response value. Thus, the liquid sample measurement device 6 can measure the glucose conversion value and the blood cell amount conversion value of blood as well as the value equivalent to the temperature of the biosensor 1 with a high accuracy using the first response value, the second response value, and the third response value.

As another method, the liquid sample measurement device 6 may refer to a plurality of first current values, a plurality of second current values, a third current value, a fourth current value, and temperatures measured by the temperature measurement units 81, 82 to obtain the concentration of glucose and the amount of blood cells of blood as well as the value equivalent, to the temperature of the biosensor 1.

Figure 38:
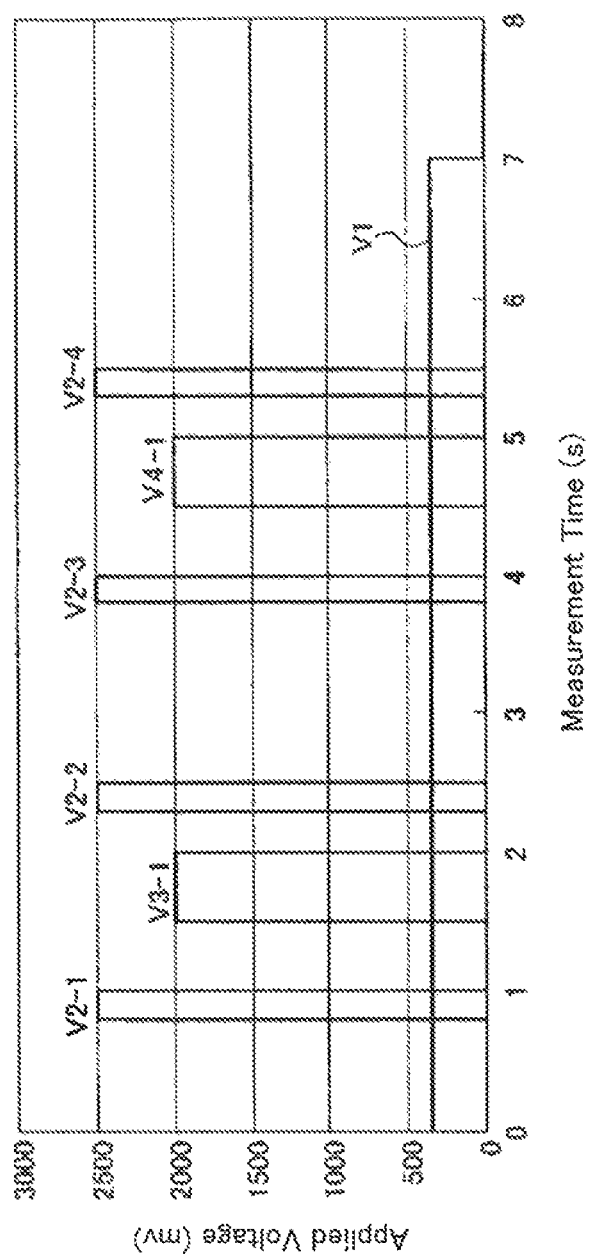
FIG. 38 is a graph showing the temporal change in voltage value in a voltage application pattern employed by a liquid sample measurement device shown as an embodiment of the present invention.

For this purpose, the CPU 74 controls, for example, the voltage value and application period of each of the first voltage, the second voltage, and the third voltage. Then, for example, while controlling each measurement timing for measuring the first current value, the second current value, and the third current value, the CPU 74 controls the measurement timing so that the first voltage is applied to measure a fourth current value at a timing different from those used for the first current value and the second current value. For example, it is desirable that the fourth current value (a fourth response value) that depends on the concentration of glucose to a high degree be obtained while the first voltage is applied. Furthermore, in order to obtain the fourth current value, for example, a fourth voltage is applied between the third counter electrode 27 and the second working electrode 23. The fourth voltage is preferably substantially equivalent to the third voltage. In this case, it is preferable that the fourth current value be measured at a timing different from those used for the first current value and the second current value, as described above as well as additionally the third current value. Specifically, for example, in FIG. 38, the fourth voltage V4-1 is applied, during which the fourth response value may be measured. When the fourth current value is used, there is an advantage that the use of respective current values obtained at different times allows information about the temporal change in, for example, temperature environment to be considered in conversion into the concentration of glucose and the amount of blood cells of blood as well as the value equivalent to the temperature of the biosensor 1.

Figure 39:
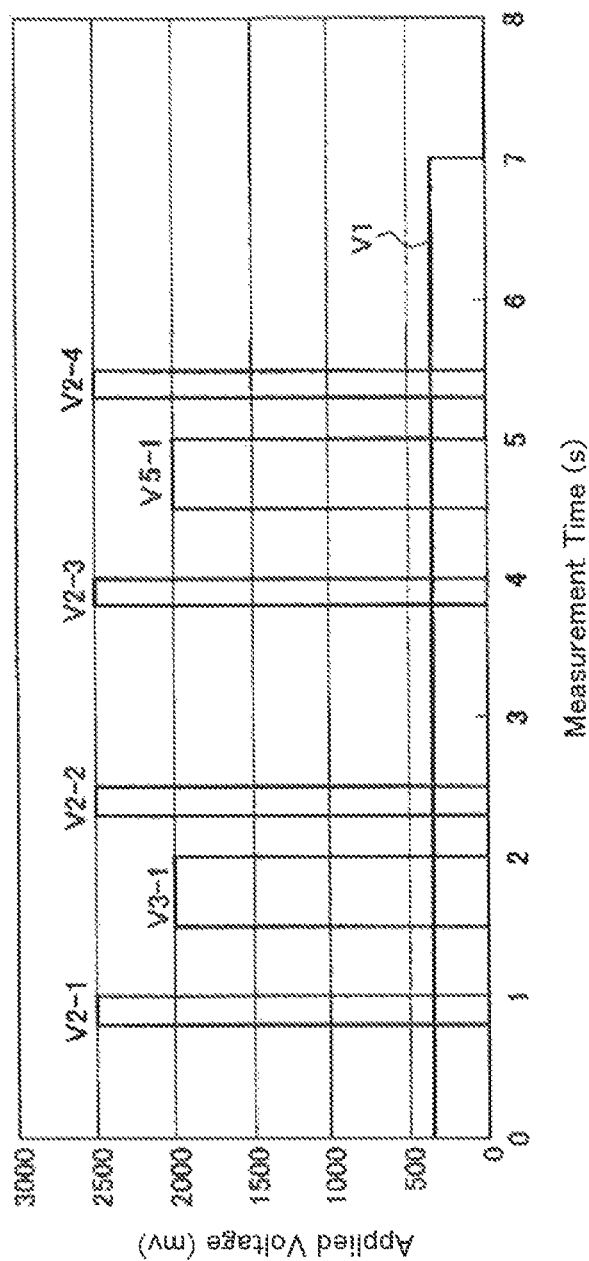
FIG. 39 is a graph showing the temporal change in voltage value in a voltage application pattern employed by a liquid sample measurement device shown as an embodiment of the present invention.

Furthermore, it is desirable that a fifth current value (a fifth response value) that depends on the temperature of the biosensor 1 to a high degree be obtained while the first voltage is applied. In order to obtain the fifth current value, for example, a fifth voltage is applied between the third counter electrode 27 (the working electrode) and the second working electrode 23 (the counter electrode). It is preferable that the fifth voltage be substantially equivalent to the third voltage. However, the third voltage V3 is applied, with the second working electrode 23(A) being used as the working electrode and the third counter electrode 27(F) being used as the counter electrode, while the fifth voltage V5 is applied, with the working electrode and the counter electrode being used inversely. It is preferable that the fifth current value (the fifth response value) be measured at a timing different from those used for the second current value and the third current value. Specifically, for example, in FIG. 39, the fifth voltage V5-1 may be applied, during which the fifth current value may be measured. There is an advantage that the use of the fifth current value also can yield results equivalent to those obtained using the third current value.

Thereafter, the CPU 74 calculates the amounts of the first component and the second component contained in the liquid as well as a first temperature equivalent value equivalent to the temperature of the biosensor 1, using, for example, a set of the first current value, the second current value, the fourth current value, and/or the fifth current value generated when the first voltage, the second voltage, and the fourth voltage were applied, respectively. This operation corresponds to a first calculation means and a first calculation step. In this case, for example, the liquid sample measurement device 6 has first recorded data stored therein in which per temperature and liquid containing the first component and the second component whose amounts are known, the first current value, the second current value, the fourth current value, and/or the fifth current value obtained using the liquid were recorded (a first storage means). Then, the first calculation means compares the first recorded data with measured data containing the first current value that was measured, the second current value that was measured, and the fourth current value and/or fifth current value that were/was measured. Then, the first calculation means can calculate the amounts of the first component and the second component of the liquid from which the recorded data most approximated to said measured data was obtained as well as the temperature of the biosensor 1 at which the recorded data most approximated to said measured data was obtained, as the amounts of the first component and the second component of the liquid introduced into the biosensor 1 as well as the first temperature equivalent value of the biosensor 1.

Moreover, the CPU 74 calculates the amounts of the first component and the second component contained in the liquid as well as a second temperature equivalent value equivalent to the temperature of the biosensor 1 using, for example, a set of the first current value, the second current value, and the third current value generated when the first voltage, the second voltage, and the third voltage were applied, respectively. This operation corresponds to a second calculation means and a second calculation step. In this case, for example, the liquid sample measurement device 6 has second recorded data stored therein including the first current value, the second current value, and the third current value recorded per temperature and liquid containing the first component and the second component whose amounts are known (a second storage means). Then, the second calculation means compares the second recorded data with measured data containing a first current value that was measured, a second current value that was measured, and a third current value that was measured. Then, the second calculation means can calculate the amounts of the first component and the second component of the liquid from which the recorded data most approximated to said measured data was obtained as well as the temperature of the biosensor 1 at which the recorded data most approximated to said measured data was obtained, a the amounts of the first component and the second component of the liquid introduced into the biosensor 1 as well as the second temperature equivalent value of the biosensor 1.

The CPU 74 recalculates the amount of the first component based on, for example, the amount of the first component calculated by the first calculation means and the amount of the first component calculated by the second calculation means. Furthermore, the CPU 74 recalculates the amount of the second component based on, for example, the amount of the second component calculated by the first calculation means and the amount of the second component calculated by the second calculation means. Moreover, the CPU 74 recalculates the temperature of the biosensor 1 based on, for example, the temperatures detected by the temperature measurement units 81, 82 as well as the first temperature equivalent value and the second temperature equivalent value of the biosensor 1. In these recalculations, for example, average values may be taken.

The liquid sample measurement device 6 can obtain the concentration of glucose (the amount of the first component) and the amount of blood cells (the amount of the second component) of blood as well as the value equivalent to the temperature of the biosensor 1 using the values obtained by the first calculation means and the second calculation means as well as the temperatures measured by the temperature measurement units 81, 82. Therefore, as described above, the liquid sample measurement device 6 can calculate the concentration of glucose (the amount of the first component) and the amount of blood cells (the amount of the second component) of blood as well as the value equivalent to the temperature of the biosensor 1 with a higher accuracy as compared to the values obtained using only the first calculation means or the second calculation means as described above.

DESCRIPTION OF THE NUMERALS

1 Biosensor
6 Liquid Sample Measurement Device
21 First Working Electrode
22 First Counter Electrode
23 Second Working Electrode
24 Second Counter Electrode
27 Third Counter Electrode
76 Data Storage Unit
81, 82 Temperature Measurement Unit

The invention claimed is:

1. A liquid sample measurement method of measuring the amounts of components using a biosensor in which a liquid is introduced and then components contained in said liquid are subjected to oxidation-reduction using an oxidoreductase,
wherein the liquid sample measurement method comprises:
a first current value measurement step for detecting, as a first current value, an oxidation-reduction current that is generated by the oxidation-reduction when a first voltage is applied to a first electrode pair that composes the biosensor;
plural second current value measurement steps for detecting, as a second current value, a current that is generated when a second voltage is applied to a second electrode pair that composes the biosensor, while the first voltage is applied to the first electrode pair;
a third current value measurement step for detecting, as a third current value, a current that is generated when a third voltage is applied to a third electrode pair that composes the biosensor, while the first voltage is applied to the first electrode pair; and
a calculation step for calculating the amounts of a first component and a second component contained in the liquid as well as a value equivalent to the temperature of the biosensor using a set of the first current value, the second current value, and the third current value generated when the first voltage, the second voltage, and the third voltage were applied, respectively,
wherein the third current value measurement step is conducted between two of the second current value measurement steps.

2. The liquid sample measurement method according to claim 1, wherein in the calculation step,
recorded data, in which per temperature and liquid containing the first component and the second component whose amounts are known, the first current value, the second current value, and the third current value obtained with respect to the liquid were recorded, is compared with measured data containing the first current value that was measured, the second current value that was measured, and the third current value that was measured, and the amount of the first component of the liquid from which the recorded data most approximated to said measured data was obtained is calculated as the amount of the first component of the liquid introduced into the biosensor.

3. The liquid sample measurement method according to claim 1, further comprising a fourth current measurement step for detecting, as a fourth current value, a current that is generated when a fourth voltage is applied to the third electrode pair that composes the biosensor, at a timing different from that at which the third current value is detected, wherein in the calculation step, the amounts of the first component and the second component contained in the liquid as well as the value equivalent to the temperature of the biosensor are calculated using the fourth current value in addition to the first current value, the second current value, and the third current value.

4. The liquid sample measurement method according to claim 1, further comprising a fifth current measurement step for detecting, as a fifth current value, a current that is generated when a fifth voltage is applied to the third electrode pair that composes the biosensor, at a timing different from those at which the second current value and the third current value are detected, wherein in the calculation step, the amounts of the first component and the second component contained in the liquid as well as the value equivalent to the temperature of the biosensor are calculated using the fifth current value in addition to the first current value, the second current value, and the third current value.

* * * * *